(12) United States Patent
Mori et al.

(10) Patent No.: US 9,808,279 B2
(45) Date of Patent: Nov. 7, 2017

(54) MEDICAL KNIFE

(75) Inventors: Makoto Mori, Seki (JP); Hidetoshi Amemoto, Seki (JP); Kazuyuki Hasebe, Seki (JP)

(73) Assignee: KAI R&D CENTER CO., LTD., Gifu-ken (JP)

( * ) Notice: Subject to any disclaimer, the term of this patent is extended or adjusted under 35 U.S.C. 154(b) by 600 days.

(21) Appl. No.: 14/110,503

(22) PCT Filed: Apr. 27, 2012

(86) PCT No.: PCT/JP2012/061406
§ 371 (c)(1),
(2), (4) Date: Oct. 8, 2013

(87) PCT Pub. No.: WO2012/147934
PCT Pub. Date: Nov. 1, 2012

(65) Prior Publication Data
US 2014/0031847 A1    Jan. 30, 2014

(30) Foreign Application Priority Data

Apr. 28, 2011   (JP) ................. 2011-100960

(51) Int. Cl.
*A61B 17/3211*   (2006.01)
*A61F 9/013*   (2006.01)

(52) U.S. Cl.
CPC ........ *A61B 17/3211* (2013.01); *A61F 9/0133* (2013.01); *F04C 2270/0421* (2013.01)

(58) Field of Classification Search
CPC ............... A61F 9/0133; A61B 17/3211; F04C 2270/0421; B26B 3/00; B26B 9/00; B26B 9/02
See application file for complete search history.

(56) References Cited

U.S. PATENT DOCUMENTS 5,002,565 A   3/1991   McGregor
5,217,476 A   6/1993   Wishinsky
(Continued)

FOREIGN PATENT DOCUMENTS

EP   1 270 534 A1   1/2003
JP   61-48713 U   4/1986
(Continued)

OTHER PUBLICATIONS

International Preliminary Report on Patentability dated Oct. 29, 2013 in corresponding International application No. PCT/JP2012/061406.
(Continued)

*Primary Examiner* — Corrine McDermott
*Assistant Examiner* — Tin Nguyen
(74) *Attorney, Agent, or Firm* — Posz Law Group, PLC

(57) ABSTRACT

A medical knife includes a blade plate and a blade portion formed at the distal end of the blade plate. Cutting edges extend from the distal end to the proximal end of the blade portion. Two blade surfaces in the width direction of a back-face portion of the blade portion are formed to gradually increase a distance between opposite side and cutting edge from one of the distal end and the proximal end to the other. The two blade surfaces in the width direction of a front-face portion of the blade portion are formed such that the distance between the opposite side and the cutting edge becomes equal in a zone corresponding to a distal end of the cutting edge and a zone corresponding to a proximal end of the cutting edge, over the entire cutting edge from the distal end to the proximal end of the cutting edge.

9 Claims, 12 Drawing Sheets

(56) References Cited

U.S. PATENT DOCUMENTS

| | | | |
|---|---|---|---|
| 5,352,233 A | | 10/1994 | Anis |
| 5,713,915 A | * | 2/1998 | Van Heugten ........ A61F 9/0133 |
| | | | 606/166 |
| 6,056,764 A | | 5/2000 | Smith |
| 6,099,543 A | | 8/2000 | Smith |
| RE37,304 E | | 7/2001 | Van Heugten et al. |
| 2001/0029386 A1 | * | 10/2001 | Matsutani ............. A61F 9/0133 |
| | | | 606/166 |
| 2004/0089159 A1 | | 5/2004 | Matsutani et al. |
| 2005/0070941 A1 | | 3/2005 | Isogimi |

FOREIGN PATENT DOCUMENTS

| | | |
|---|---|---|
| JP | 07-500029 A | 1/1995 |
| JP | 2001-238890 A | 9/2001 |
| JP | 2005-013379 A | 1/2005 |
| JP | 2005-103035 A | 4/2005 |
| JP | 2005-334054 A | 12/2005 |
| JP | 3120743 U | 3/2006 |
| JP | 4226429 B2 | 2/2009 |
| WO | 93/01755 A1 | 2/1993 |
| WO | 94/17740 A1 | 8/1994 |

OTHER PUBLICATIONS

International Search Report of the International Searching Authority dated Aug. 7, 2012 for the corresponding international application No. PCT/JP2012/061406 (with English translation).
Extended European Search Report dated Aug. 19, 2014 in corresponding EP application No. 12776663.2.

* cited by examiner

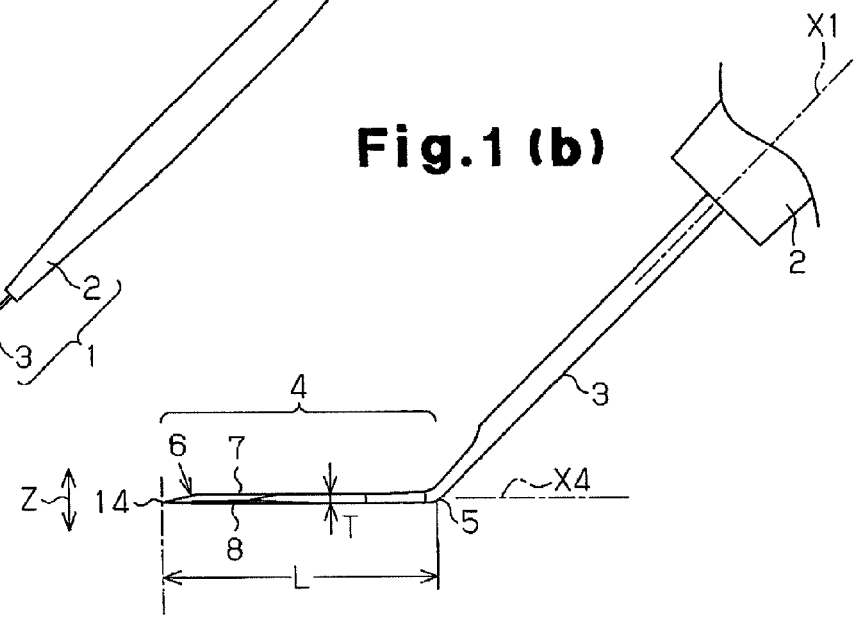
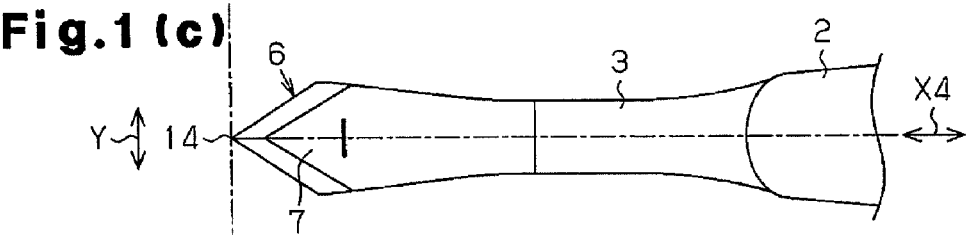
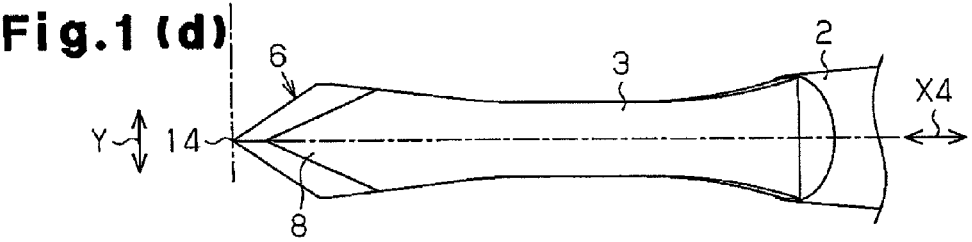
Fig.1 (a)
Fig.1 (b)
Fig.1 (c)
Fig.1 (d)

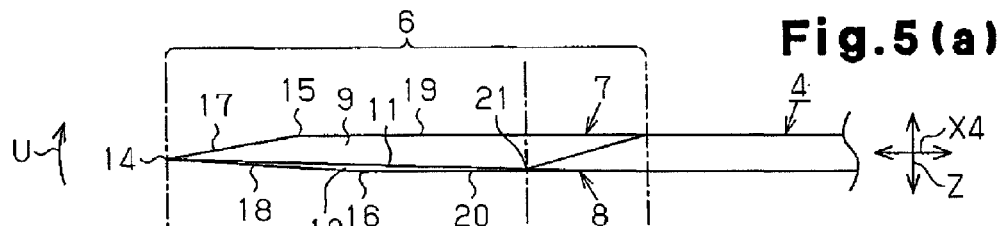
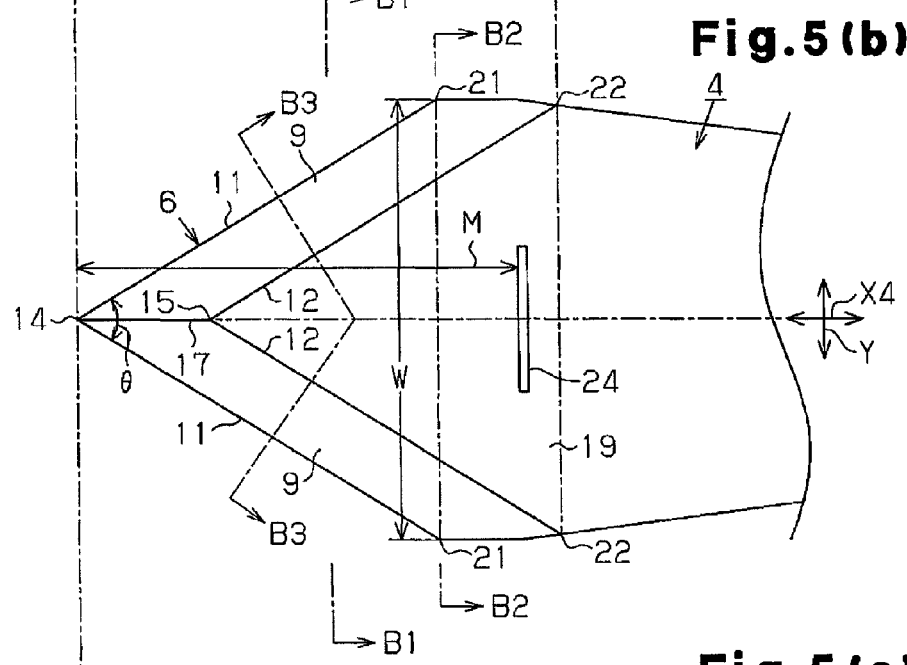
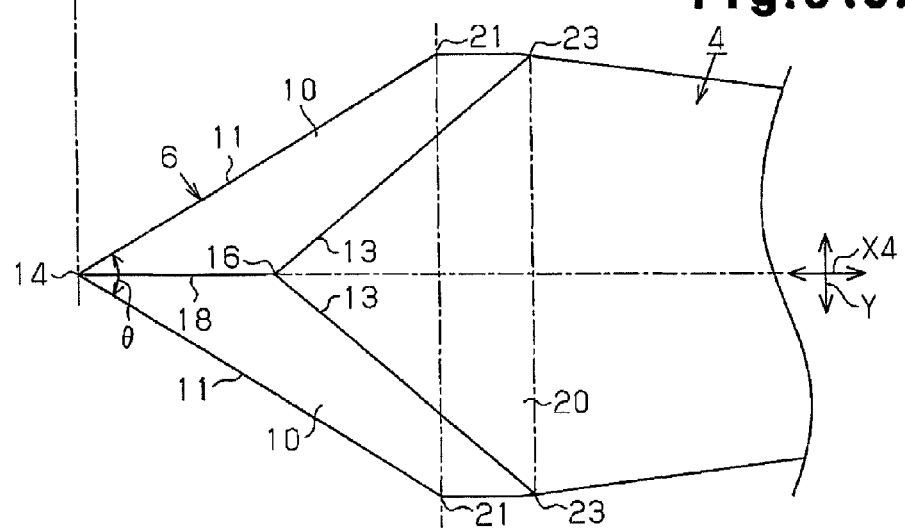

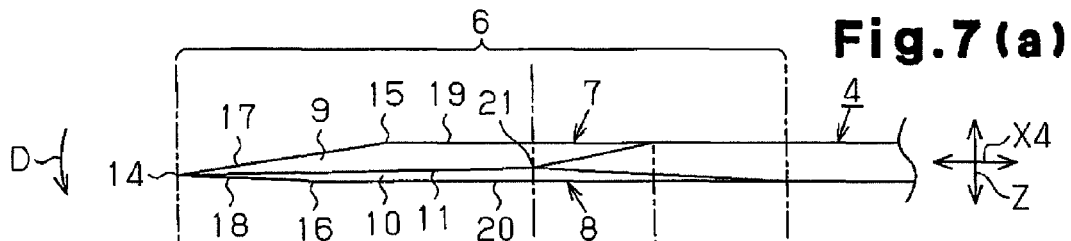

MEDICAL KNIFE

CROSS REFERENCE TO RELATED APPLICATIONS

This application is a U.S. national stage application of PCT/JP2012/061406 filed on Apr. 27, 2012 and is based on Japanese Patent Application No. 2011-100960 filed on Apr. 28, 2011, the disclosure of which is incorporated herein by reference.

FIELD OF THE INVENTION

The present invention relates to a medical knife serving as a cutting tool for various types of surgeries, which is used to cut body tissue such as the eyeball in, for example, cataract surgery.

BACKGROUND OF THE INVENTION

For conventional cataract surgeries, the corneal incision method and the scleral incision method are generally known. In the corneal incision method, the operator uses a single knife such as a slit knife or a clear corneal knife to form an incision wound in the cornea and then sends the knife into the anterior chamber. In the scleral incision method, the operator cuts the cornea and then performs lamellar scleral dissection using a straight knife. Subsequently, the operator extends the incision wound to the cornea using a crescent knife and, eventually, introduces a slit knife into the anterior chamber. As a new incision method having advantages of the corneal and scleral incision methods, the transconjunctival single-plane sclerocorneal incision method is now known. In the transconjunctival single-plane sclerocorneal incision method, as illustrated in FIGS. 4(a) and 4(b), for example, the operator introduces a knife into a conjunctiva 32 at a position spaced outward, which is, for example, toward the eyebrow, from a limbus 31 by approximately 0.5 mm, and then sends the knife directly into a sclera 33. The knife is then sent into a cornea 34 until it reaches an anterior chamber 35. If a knife is introduced into the conjunctiva 32 at a position close to the eyebrow, the incision wound is covered and protected by the upper eyelid after the surgery. This reduces the changes of endophthalmitis caused by infection. Until the knife reaches the stromal layer of the cornea 34, the operator moves the knife upward, which is outward, along the curve of the cornea 34. To send the knife into the anterior chamber 35, the knife is faced slightly downward (inward) and moved parallel to or slightly upward (outward) with respect to an iris 36. This makes it easier to form a substantially linear inner incision line 37a of an incision wound 37. Then, the operator cuts the conjunctiva 32 upward to the cornea 34 at the opposite ends of a wound 37b (an outer incision line) of the incision wound 37. This allows perfusion fluid to flow to the sides of the wound 37b (the outer incision line), thus preventing the perfusion fluid from flowing into the conjunctiva 32 and causing conjunctival chemosis. As a result, as viewed along the cross section of the eyeball shown in FIG. 4(a), the knife proceeds along a substantially S-shaped movement path 38 by changing its proceeding direction sequentially through a movement path section 38a extending in the direction of arrow P to enter the conjunctiva 32, a movement path section 38b extending in the direction of arrow Q to proceed from the sclera 33 into the cornea 34, and a movement path section 38c extending in the direction of arrow R to enter the anterior chamber 35. The above-described incision methods have the advantages and disadvantages listed in Table 1. Particularly, the scleral incision method and the transconjunctival single-plane sclerocorneal incision method form a substantially cranked or S-shaped path to form the incision wound 37. This allows the incision wound 37 to naturally close without being sutured, exhibiting improved self-sealing performance.

TABLE 1

| | Corneal Incision | Transconjunctival Single-plane sclerocorneal Incision | Scleral Incision |
|---|---|---|---|
| Damage to Conjunctiva | None | Minimal (Incision Only) | Observed (Incision And Detachment) |
| Damage to Sclera | None | Minimal (Ablation Not Performed) | Observed (Ablation And Hemostasis) |
| Damage to Cornea | Observed | Minimal | |
| Conjunctival Chemosis | None | Extremely Low Level | Rare Even In Wider Range of Conjunctival Detachment |
| Operation Time | | Short | Long |
| Tunnel Length | Short | Medium | Long |
| Tunnel Shape | Linear | Slightly Curved | Curved |
| Self-Sealing Performance | Normal | Improved (Cornea Covering Wound And Blood Functioning Glue) | |

Conventionally, a medical knife used in a cataract surgery according to the transconjunctival single-plane sclerocorneal incision method includes a handle extending from a proximal end of a blade plate having a distal blade portion, as in, for example, a bevel-up type slit knife or the knife shown in FIG. 1, particularly, out of the attached drawings of Patent Document 1, which will be listed below. In this knife, the extending direction of the grip portion of the handle and the extending direction of the blade plate cross each other. As illustrated in FIGS. 2 and 5, particularly, of Patent Document 1, the blade portion of the blade plate has a front-face portion and a back-face portion. The front-face portion is formed on the upper side in the thickness direction of the blade plate, which corresponds to the extending direction of the grip portion of the handle. The back-face portion is formed on the lower side in the thickness direction of the blade plate, which faces opposite to the extending direction of the grip portion of the handle. Two blade surfaces are formed on the opposite sides in the width direction of the blade plate, which crosses the thickness direction of the blade plate, at the front-face portion and the back-face portion of the blade portion. The blade surfaces are both inclined from the middle portion in the width direction of the blade plate toward the opposite outer ends in the width direction to decrease the interval in the thickness direction. A cutting edge is formed at the outer end at which the blade surfaces of the front-face portion cross the corresponding blade surfaces of the back-face portion and extends from the distal end of the blade portion to the proximal end of the blade portion.

In a typical cataract surgery using the above-described transconjunctival single-plane sclerocorneal incision method using the medical knife according to Patent Document 1 or the like, the operator introduces the knife into the anterior chamber 35 along the movement path section 38c, which extends in the direction of arrow R, as illustrated in FIG. 4(a). At this stage, when reactive force to the force acting in the proceeding direction of the knife is applied to the blade portion, the front-face portion of the blade portion and the back-face portion of the blade portion receive the upward force that presses the blade portion upward and the downward force that presses the blade portion downward in correspondence with the shape of the front-face portion and the shape of the back-face portion. The blade portion enters the anterior chamber 35 while being translated upward or downward in correspondence with equilibrium between the upward force and the downward force. If the blade portion is translated downward, the point at which the opposite cutting edges in the width direction cross each other facilitates formation of the inner incision line 37c in a projected shape, with reference to FIG. 4(c). If the blade portion is translated upward, as shown in FIG. 4(d), formation of the inner incision line 37d in a V shape is facilitated. In both cases, the inner incision lines 37c, 37d are easily displaced offset from each other, and the above-described self-sealing performance is hampered disadvantageously.

PRIOR ART DOCUMENT

Patent Document

Patent Document 1: Japanese Patent No. 4226429

As shown in, particularly, FIGS. 2 and 5 of Patent Document 1, the two blade surfaces in the width direction of the front-face portion are formed to gradually increase the distance between the opposite sides with respect to the cutting edge from the distal end toward the proximal end. With reference to FIG. 2 of Patent Document 1, the two blade surfaces in the width direction of the back-face portion are formed to have a uniform distance between the opposite sides with respect to the cutting edge throughout the range corresponding to the cutting edge from the distal end to the proximal end of the cutting edge. With reference to FIG. 5 of Patent Document 1, the two blade surfaces in the width direction of the back-face portion are formed to gradually increase the distance between the opposite sides with respect to the cutting edge from the distal end to the proximal end, as in the blade surfaces in the width direction of the front-face portion.

In the medical knife shown in FIG. 2 of Patent Document 1, the surface area of each blade surface in the width direction of the front-face portion of the blade portion is great at the proximal end compared to the distal end. Accordingly, when the downward force pressing the blade portion downward acts on the front-face portion, as has been described, the downward force acts on the proximal end of the front-face portion more intensely than the distal end of the front-face portion. Such unevenly acting downward force easily generates rotation moment acting in such a direction to press the proximal end of the blade portion downward and the distal end of the blade portion upward. However, the surface area of each blade surface in the width direction of the back-face portion of the blade portion is uniform from the distal end to the proximal end. The upward force that presses the blade portion upward is therefore unlikely to act unevenly and produce rotation moment. This is disadvantages for switching from the movement path section 38b extending in the direction of arrow Q to proceed from the sclera 33 to the cornea 34 to the movement path section 38c extending in the direction of arrow R to enter the anterior chamber 35, with reference to FIG. 4(a), in the above-described substantially S-shaped movement path 38.

In contrast, in the medical knife shown in FIG. 5 of Patent Document 1, the surface area of each blade surface in the width direction of the front-face portion of the blade portion is great at the proximal end compared to the distal end. Accordingly, when the above-described downward force pressing the blade portion downward acts on the front-face portion, the downward force acts more intensely on the proximal end of the front-face portion than the distal end of the front-face portion. Such unevenly acting downward force easily generates rotation moment acting in such a direction to press the proximal end of the blade portion downward and the distal end of the blade portion upward. Also, the surface area of each blade surface in the width direction of the back-face portion of the blade portion is great at the proximal end compared to the distal end. As a result, when the above-described upward force pressing the blade portion upward acts on the back-face portion, the upward force acts more intensely on the proximal end of the back-face portion than the distal end of the back-face portion. Such unevenly acting downward force easily generates rotation moment acting in such a direction to press the proximal end of the blade portion upward and the distal end of the blade portion downward. As a result, the rotation moments equilibrate with each other, and the rotation moments are not generated in the blade portion. This is disadvantageous for switching among the movement path sections 38a, 38b, 38c in the above-described S-shaped movement path 38.

SUMMARY OF THE INVENTION

Accordingly, it is an objective of the present invention to improve the shape of a blade portion of a medical knife to facilitate formation of a substantially S-shaped incision wound with improved self-sealing performance in, for example, a cataract surgery using the transconjunctival single-plane sclerocorneal incision method.

First to sixth aspects of the present invention will now be described.

The medical knives according to the first to sixth aspects have a common configuration as described below.

The medical knives each include a handle having a grip portion and extending in one direction, a blade plate, and a blade portion. The blade plate extends from the handle in a manner intersecting the handle and includes a distal end and a proximal end. The blade portion is formed at the distal end of the blade plate. The blade portion has a front-face portion and a back-face portion. The front-face portion is formed on an upper side in the thickness direction of the blade plate where the grip portion is arranged. The back-face portion is formed on a lower side in the thickness direction of the blade plate opposite to the grip portion. Blade surfaces are formed at opposite sides in the width direction of the blade plate intersecting the thickness direction of the blade portion in both the front-face portion and the back-face portion of the blade portion. The blade surfaces are inclined from a middle portion in the width direction to opposite outer ends in the width direction in the blade plate to cooperatively decrease a thickness dimension. An outer end at which each one of the blade surfaces of the front-face portion and the corresponding one of the blade surfaces of the back-face portion cross each other form a cutting edge extending from the distal end to the proximal end of the blade portion.

In a first aspect of the invention, in the blade portion having the two blade surfaces in the width direction of the front-face portion and the two blade surfaces in the width direction of the back-face portion, the blade surfaces in the width direction of the back-face portion are each shaped to gradually increase the distance between the opposite side and the cutting edge from one of the distal end and the proximal end to the other. In other words, the blade surfaces in the width direction of the back-face portion are gradually widened from the distal end to the proximal end, as shown in the first embodiment illustrated in FIGS. 1 to 4. In the second embodiment illustrated in FIGS. 5 and 6, each blade surface in the width direction of the back-face portion is gradually enlarged from the proximal end to the distal end. The blade surfaces in the width direction of the front-face portion are shaped such that the distance between the opposite side and the cutting edge becomes equal at the distal end and the proximal end throughout the range corresponding to the cutting edge from the distal end to the proximal end of the cutting edge. Specifically, the term "equal" herein includes the state of being substantially equal.

In a second aspect of the invention, in the blade portion having the two blade surfaces in the width direction of the front-face portion and the two blade surfaces in the width direction of the back-face portion, the blade surfaces in the width direction of the back-face portion are shaped to gradually increase the distance between the opposite side and the cutting edge from one of the distal end and the proximal end to the other. The blade surfaces in the width direction of the front-face portion are shaped to gradually decrease the distance between the opposite side and the cutting edge from one of the distal end and the proximal end to the other, in the opposite direction to the direction in which the distance between the opposite side and the cutting edge increases on each blade surface in the width direction of the back-face portion. In other words, as shown in the third embodiment in FIGS. 7 and 8, each blade surface in the width direction of the back-face portion is gradually enlarged from the distal end to the proximal end and each blade surface in the width direction of the front-face portion is gradually enlarged from the proximal end to the distal end. Alternatively, with reference to the fourth embodiment illustrated in FIGS. 9 and 10, each blade surface in the width direction of the back-face portion is gradually enlarged from the proximal end to the distal end and each blade surface in the width direction of the front-face portion is gradually enlarged from the distal end to the proximal end.

In a third aspect corresponding to the fifth embodiment shown in FIGS. 11 and 12, in the blade portion having the two blade surfaces in the width direction of the front-face portion and the two blade surfaces in the width direction of the back-face portion, the blade surfaces in the width direction of the back-face portion are shaped such that the distance between the opposite side and the cutting edge becomes equal at the distal end and the proximal end throughout the range corresponding to the cutting edge from the distal end to the proximal end of the cutting edge. The blade surfaces in the width direction of the front-face portion are each shaped to gradually increase the distance between the opposite side and the cutting edge from the proximal end to the distal end. Specifically, the term "equal" herein includes the state of being substantially equal.

In the first aspect corresponding to the first embodiment illustrated in FIGS. 1 to 4, the third aspect corresponding to the third embodiment shown in FIGS. 7 and 8, and the third aspect corresponding to the fifth embodiment illustrated in FIGS. 11 and 12, a cataract surgery using the transconjunctival single-plane sclerocorneal incision method is carried out by the operator by moving the blade portion along a substantially S-shaped movement path from the vicinity of the limbus to the anterior chamber through the conjunctiva, the sclera, and the cornea. In the surgery, rotation moment is easily produced in a direction in which the proximal end of the blade portion is pressed upward and the distal end of the blade portion is pressed downward. The blade portion is thus smoothly moved from the movement path section proceeding from the sclera to the cornea to the movement path section entering the anterior chamber with less resistance. As a result, a substantially S-shaped incision wound exhibiting improved self-sealing performance is easily formed. Also, the inner incision line of the incision wound is prevented from having a projected shape and easily formed in a linear shape.

In the first aspect corresponding to the second embodiment illustrated in FIGS. 5 and 6 and the second aspect corresponding to the fourth embodiment shown in FIGS. 9 and 10, a cataract surgery using the transconjunctival single-plane sclerocorneal incision method is performed by the operator by moving the blade portion along the substantially S-shaped movement path from the vicinity of the limbus to the anterior chamber via the conjunctiva, the sclera, and the cornea. In the surgery, rotation moment is easily generated in a direction in which the distal end of the blade portion is pressed upward and the proximal end of the blade portion is pressed downward. This allows the blade portion to smoothly move from the movement path section entering the conjunctiva to the movement path section proceeding from the sclera to the cornea with less resistance. As a result, a substantially S-shaped incision wound exhibiting improved self-sealing performance is easily formed.

In the first aspect (corresponding to the first and second embodiments illustrated in FIGS. 1 to 8), each blade surface in the width direction of the front-face portion is shaped to have a uniform distance between the opposite side and the cutting edge throughout the range corresponding to the cutting edge from the distal end to the proximal end of the cutting edge. The term "uniform" herein includes the state of being substantially uniform. As a result, in the first aspect corresponding to the first embodiment shown in FIGS. 1 to 4, rotation moment is easily generated in a direction in which the proximal end of the blade portion is pressed upward and the distal end of the blade portion is pressed downward. Also, in the first aspect corresponding to the second embodiment illustrated in FIGS. 5 and 6, rotation moment is easily produced in a direction in which the distal end of the blade portion is pressed upward and the proximal end of the blade portion is pressed downward.

In the third aspect (corresponding to the fifth embodiment illustrated in FIGS. 11 and 12), each blade surface in the width direction of the back-face portion is shaped to have a uniform distance between the opposite side and the cutting edge throughout the range corresponding to the cutting edge from the distal end to the proximal end of the cutting edge. The term "uniform" herein includes the state of being substantially uniform. As a result, rotation moment is easily generated in direction D, in which the proximal end of the blade portion 6 is pressed upward and the distal end of the blade portion 6 is pressed downward.

In the front-face portion and the back-face portion of the blade portion in the first to third aspects (corresponding to the first to fifth embodiments), the boundary between the blade surfaces in the width direction is formed between the point at which the cutting edges of the blade surfaces in the width direction cross each other and the peak at which the opposite sides of the blade surfaces in the width direction cross each other. A middle surface extends between the opposite sides of the blade surfaces in the width direction. As a result, in a cataract surgery using the transconjunctival single-plane sclerocorneal incision method, the operator easily moves the blade portion along the substantially S-shaped movement path from the vicinity of the limbus to the anterior chamber via the conjunctiva, the sclera, and the cornea.

In the blade plate in the first to third aspects (corresponding to the first to fifth embodiments), each cutting edge in the width direction of the blade portion extends from the point to an end. The maximum width-direction distance is defined between the ends of the cutting edges in the width direction. A mark is formed on a line segment connecting the ends of the cutting edges in the width direction to each other or on the proximal or distal side with respect to the line segment. The distance between the mark and the point and the width-direction distance between the ends of the cutting edges in the width direction are equal to each other. The term "equal" herein includes the state of being substantially equal. As a result, in a cataract surgery using the transconjunctival single-plane sclerocorneal incision method, in which the operator moves the blade portion along the substantially S-shaped path from the vicinity of the limbus to the anterior chamber via the conjunctiva, the sclera, and the cornea, the point of the blade portion enters the anterior chamber exactly when the mark reaches the outer incision line of the incision wound. As the operator further moves the blade portion, the incision wound, which is formed between the inner incision line and the outer incision line, is shaped nearly as a square and thus given improved self-sealing performance.

In the blade plate in the fourth aspect (corresponding to the first to fifth embodiments), each cutting edge in the width direction of the blade portion extends from the point to an end. The maximum width-direction distance is defined between the ends of the cutting edges in the width direction. A mark is formed on a line segment connecting the ends of the cutting edges in the width direction to each other or on the proximal or distal side with respect to the line segment. The distance between the mark and the point and the width-direction distance between the ends of the cutting edges in the width direction are equal to each other. The term "equal" herein includes the state of being substantially equal. As a result, in a cataract surgery using the transconjunctival single-plane sclerocorneal incision method, in which the operator moves the blade portion along the substantially S-shaped path from the vicinity of the limbus to the anterior chamber via the conjunctiva, the sclera, and the cornea, the point of the blade portion enters the anterior chamber exactly when the mark reaches the outer incision line of the incision wound. As the operator further moves the blade portion, the incision wound, which is formed between the inner incision line and the outer incision line, is shaped nearly as a square and thus given improved self-sealing performance.

In the fifth aspect (corresponding to the first to fifth embodiments), the blade plate is bent toward the front-face portion of the blade portion with respect to the handle. The length of the blade plate from the distal end to the proximal end of the blade portion is set to a value not less than ten times and not more than fifty times the thickness of the blade plate. As a result, in a cataract surgery using the transconjunctival single-plane sclerocorneal incision method, in which the operator moves the blade portion along the substantially S-shaped movement path from the vicinity of the limbus to the anterior chamber via the conjunctiva, the sclera, and the cornea, flexing of the blade plate is regulated so that the blade plate is easier to manipulate.

In the sixth aspect (corresponding to the first to fifth embodiments), the separation angle between the cutting edges in the width direction of the blade portion is set to a value not less than 60 degrees and not more than 120 degrees and, preferably, a value not less than 60 degrees and not more than 90 degrees. The separation angle between the cutting edges in the width direction is thus an obtuse angle. As a result, the inner incision line of the incision wound is prevented from having a projected shape and is easily formed in a linear shape.

In the first to third aspects (corresponding to the first to fifth embodiments), the middle surface of the front-face portion of the blade portion and the middle surface of the back-face portion of the blade portion may be formed parallel to each other. In this case, in a cataract surgery using the transconjunctival single-plane sclerocorneal incision method, the operator receives less resistance when moving the blade portion along the substantially S-shaped movement path 38 from the vicinity of the limbus 31 to the anterior chamber via the conjunctiva, the sclera, and the cornea.

In the front-face portion and the back-face portion of the blade portion in the first to third aspects (corresponding to the first to fifth embodiments), the blade surfaces in the width direction may be shaped symmetrical with respect to a plane in the thickness direction including the boundary between the blade surfaces in the width direction. In this case, in a cataract surgery using the transconjunctival single-plane sclerocorneal incision method, the operator is allowed to move the blade portion along the substantially S-shaped movement path from the vicinity of the limbus 31 to the anterior chamber via the conjunctiva, the sclera, and the cornea in a well-balanced manner in the width direction.

In the first to third aspects (corresponding to the first to fifth embodiments), each blade surface of the front-face portion of the blade portion and each blade surface of the back-face portion of the blade portion may be shaped differently from each other. This is likely to generate rotation moment in a direction in which the proximal end of the blade portion is pressed upward and the distal end of the blade portion is pressed downward or a direction in which the distal end of the blade portion is pressed upward and the proximal end of the blade portion is pressed downward.

In the first to third aspects (corresponding to the first to fifth embodiments), one of the inclination angle α between each blade surface of the front-face portion of the blade portion and a plane including the cutting edges in the width direction and the inclination angle between each blade surface of the back-face portion of the blade portion and the plane including the cutting edges in the width direction may be greater than the other. This is likely to generate rotation moment in a direction in which the proximal end of the blade portion is pressed upward and the distal end of the blade portion is pressed downward or a direction in which the distal end of the blade portion is pressed upward and the proximal end of the blade portion is pressed downward.

Alternatively, one of the inclination angle of each blade surface of the front-face portion of the blade portion and the inclination angle of each blade surface 10 of the back-face portion of the blade portion may be set to a value not more than a half of the other. This is further likely to generate rotation moment in a direction in which the proximal end of the blade portion is pressed upward and the distal end of the blade portion is pressed downward or a direction in which the distal end of the blade portion is pressed upward and the proximal end of the blade portion 6 is pressed downward.

In the first to third aspects (corresponding to the first to fifth embodiments), the blade plate may be bent toward the front-face portion of the blade portion with respect to the handle. The length of the blade plate from the distal end to the proximal end of the blade portion may be set to a value not less than ten times and not more than fifty times the thickness of the blade plate. As a result, in a cataract surgery using the transconjunctival single-plane sclerocorneal incision method, in which the operator moves the blade portion along the substantially S-shaped movement path from the vicinity of the limbus to the anterior chamber via the conjunctiva, the sclera, and the cornea, flexing of the blade plate 4 is regulated so that the blade plate 4 is easier to manipulate.

In the first to third aspects (corresponding to the first to fifth embodiments), the separation angle between the cutting edges in the width direction of the blade portion is set to a value not less than 60 degrees and not more than 120 degrees and, preferably, a value not less than 60 degrees and not more than 90 degrees. In the seventeenth invention, the separation angle between the cutting edges 11 in the width direction is an obtuse angle. As a result, the inner incision line of the incision wound is prevented from having a projected shape and easily formed in a linear shape.

In the front-face portion and the back-face portion of the blade portion in the first aspect (corresponding to the first and second embodiments), the boundary between the blade surfaces in the width direction is formed between the point at which the cutting edges of the blade surfaces in the width direction cross each other and the peak at which the opposite sides of the blade surfaces in the width direction cross each other. A middle surface extends between the opposite sides of the blade surfaces in the width direction. The distance between the opposite side and the cutting edge in each blade surface in the width direction of the back-face portion of the blade portion may be greater than the distance between the opposite side and the cutting edge in each blade surface in the width direction of the front-face portion of the blade portion. In this case, in a cataract surgery using the transconjunctival single-plane sclerocorneal incision method, the operator is allowed to move the blade portion easily along the substantially S-shaped movement path from the vicinity of the limbus to the anterior chamber via the conjunctiva, the sclera, and the cornea. Also, the blade surfaces in the width direction of the back-face portion of the blade portion, compared to the blade surfaces in the width direction of the front-face portion of the blade portion, is likely to influence generation of rotation moment in a direction in which the proximal end of the blade portion is pressed upward and the distal end of the blade portion is pressed downward or a direction in which the distal end of the blade portion is pressed upward and the proximal end of the blade portion 6 is pressed downward.

EFFECTS OF THE INVENTION

The present invention provides a medical knife having a blade portion with an improved shape. The medical knife easily forms a substantially S-shaped incision wound 37 exhibiting enhanced self-sealing performance in, for example, a cataract surgery using the transconjunctival single-plane sclerocorneal incision method.

BRIEF DESCRIPTION OF THE DRAWINGS

FIG. 1(*a*) is a front view showing a medical knife according to a first embodiment of the present invention;

FIG. 1(*b*) is an enlarged front view showing a portion of FIG. 1(*a*);

FIG. 1(*c*) is an enlarged plan view showing a portion of FIG. 1(*a*);

FIG. 1(*d*) is an enlarged bottom view showing a portion of FIG. 1(*a*);

FIG. 2(*b*) is an enlarged view showing a portion of FIG. 1(*c*) corresponding to a front side of a blade portion;

FIG. 2(*c*) is an enlarged view showing a portion of FIG. 1(*d*) corresponding to a back side of the blade portion;

FIG. 3(*b*) is a cross-sectional view taken along line A2-A2 of FIG. 2(*b*);

FIG. 3(*c*) is a cross-sectional view taken along line A3-A3 of FIG. 2(*b*);

FIGS. 4(*b*), 4(*c*), and 4(*d*) are surface views each showing a portion of a limbus of the eyeball;

FIG. 5(*a*) is an enlarged front view showing a portion of a blade portion of a medical knife according to a second embodiment of the invention;

FIG. 5(*b*) is an enlarged plan view showing a portion corresponding to a front side of the blade portion;

FIG. 5(*c*) is an enlarged bottom view showing a portion corresponding to a back side of the blade portion;

FIG. 6(*b*) is a cross-sectional view taken along line B2-B2 of FIG. 5(*b*);

FIG. 6(*c*) is a cross-sectional view taken along line B3-B3 of FIG. 5(*b*);

FIG. 7(*a*) is an enlarged front view showing a portion of a blade portion of a medical knife according to a third embodiment of the invention;

FIG. 7(*b*) is an enlarged plan view showing a portion corresponding to a front side of the blade portion;

FIG. 7(*c*) is an enlarged bottom view showing a portion corresponding to a back side of the blade portion;

FIG. 8(*b*) is a cross-sectional view taken along line C2-C2 of FIG. 7(*b*);

FIG. 8(*c*) is a cross-sectional view taken along line C3-C3 of FIG. 7(*b*);

FIG. 9(*b*) is an enlarged plan view showing a portion corresponding to a front side of the blade portion;

FIG. 9(*c*) is an enlarged bottom view showing a portion corresponding to a back side of the blade portion;

FIG. 10(*b*) is a cross-sectional view taken along line D2-D2 of FIG. 9(*b*);

FIG. 10(*c*) is a cross-sectional view taken along line D3-D3 of FIG. 9(*b*);

FIG. 11(*b*) is an enlarged plan view showing a portion corresponding to a front side of the blade portion;

FIG. 11(c) is an enlarged bottom view showing a portion corresponding to a back side of the blade portion;

DETAILED DESCRIPTION OF THE PREFERRED EMBODIMENTS

Figure 2A:
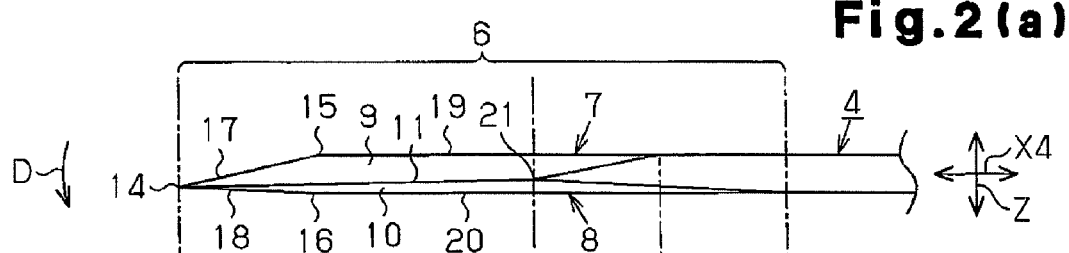
FIG. 2(*a*) is an enlarged view showing a portion of FIG. 1(*b*)

A medical knife according to a first embodiment of the present invention will now be described with reference to FIGS. 1 to 4.

A medical knife illustrated in FIG. 1(a) serves as a cutting tool for various types of surgeries, which is used to cut body tissue such as the eyeball mainly in a cataract surgery. The medical knife has a handle 1, which includes a grip portion 2 formed of plastic and a support plate 3 formed of metal such as stainless steel, and a blade plate 4 extending from the handle 1. The blade plate 4 is formed of metal such as stainless steel. As shown in FIG. 1(b), the support plate 3 is fixedly inserted into a distal end of the grip portion 2. The support plate 3 and the grip portion 2 extend in a common extending direction X1. The blade plate 4 is extended continuously from and integrally with the support plate 3. The blade plate 4 is bent at a bent portion 5, which is formed in a proximal end of the blade plate 4, with respect to the support plate 3. The extending direction X1 of the grip portion 2 and the support plate 3 of the handle 1 cross an extending direction X4 of the blade plate 4 by 45 degrees. With reference to FIGS. 1(c) and 1(d), a blade portion 6 is formed in a distal end of the blade plate 4. The blade portion 6 of the blade plate 4 includes a front-face portion 7 and a back-face portion 8. The front-face portion 7 is formed at the upper side with respect to the thickness direction Z of the blade plate 4, which corresponds to the extending direction of the grip portion 2 and the support plate 3 of the handle 1, or the bending direction. The back-face portion 8 is formed at the lower side with respect to the thickness direction Z of the blade plate 4, which is opposite to the extending direction of the grip portion 2 and the support plate 3 of the handle 1.

As illustrated in FIGS. 2(a), 2(b), 2(c), 3(a), 3(b), and 3(c), the front-face portion 7 and the back-face portion 8 of the blade portion 6 have flat blade surfaces 9 and flat blade surfaces 10, respectively, which are arranged at opposite sides in the width direction Y of the blade plate 4, which crosses the thickness direction Z. The blade surfaces 9, 10 are inclined from the middle portion in the width direction Y of the blade plate 4 to opposite outer ends in the width direction Y to decrease the dimension in the thickness direction Z. Cutting edges 11, each of which extends linearly from a distal end to a proximal end of the blade portion 6, are formed at the outer end at which the blade surfaces 9 of the front-face portion 7 cross the corresponding blade surfaces 10 of the back-face portion 8. Each of the blade surfaces 9 of the front-face portion 7 has an opposite side 12 with respect to the cutting edge 11 and each of the blade surfaces 10 of the back-face portion 8 includes an opposite side 13 with respect to the cutting edge 11. The opposite sides 12, 13 extend linearly from the distal end to the proximal end of the blade portion 6. In the front-face portion 7 of the blade portion 6, a boundary 17 between the blade surfaces 9 in the width direction Y extends linearly between a point 14 (corresponding to the distal ends of the blade plate 4 and the blade portion 6), at which the cutting edges 11 of the blade surfaces 9 cross each other in a V shape in the width direction Y, and a peak 15, at which the opposite sides 12 of the blade surfaces 9 cross each other in a V shape in the width direction Y. In the back-face portion 8 of the blade portion 6, a boundary 18 between the blade surfaces 10 in the width direction Y extends linearly between the point 14 and a peak 16, at which the opposite sides 13 of the blade surfaces 10 cross each other in a V shape in the width direction Y. A flat middle surface 19 is formed between the opposite sides 12 of the blade surfaces 9 in the width direction Y. A flat middle surface 20 is formed between the opposite sides 13 of the blade surfaces 10 in the width direction Y. Each of the middle surfaces 19, 20 is shaped each as an isosceles triangle by which the peak 15, 16 of the opposite sides 12, 13 is connected to ends 22, 23 of the opposite sides 12, 13. The proximal end of the blade portion 6 corresponds to the line segment connecting the ends 23 of the opposite sides 13 to each other, which is more spaced from the point 14 than the line segment between the ends 22 of the opposite sides 12. The middle surface 19 of the front-face portion 7 of the blade portion 6 extends parallel to the middle surface 20 of the back-face portion 8. The two cutting edges 11 in the width direction Y are gradually inclined from the back-face portion 8 to the front-face portion 7 in the direction from the point 14 to ends 21. In the front-face portion 7 of the blade portion 6, the blade surfaces 9 in the width direction Y are shaped symmetric with respect to a plane in the thickness direction that includes the boundary 17 between the blade surfaces 9 in the width direction Y. In the back-face portion 8 of the blade portion 6, the blade surfaces 10 in the width direction Y are shaped symmetric with respect to a plane in the thickness direction that includes the boundary 18 between the blade surfaces 10 in the width direction Y.

Each blade surface 10 in the width direction Y of the back-face portion 8 of the blade portion 6 is formed to gradually increase the distance G10 between the opposite side 13 and the cutting edge 11 from the distal end to the proximal end of the blade portion 6. It is preferable that the distance G10 be set to a value not less than 0.2 mm and not more than 1.5 mm at the distal end of the blade portion 6 and a value not less than 0.3 mm and not more than 2.0 mm at the proximal end of the blade portion 6. In the first embodiment, the distance G10 is set to, for example, 0.44 mm at the distal end of the blade portion 6 and 0.63 mm at the proximal end of the blade portion 6. In the front-face portion 7 of the blade portion 6, each blade surface 9 in the width direction Y is formed to have a substantially uniform distance G9 between the opposite side 12 and the cutting edge 11 throughout the range corresponding to the cutting edge 11 from the distal end to the proximal end of the blade portion 6. It is preferable that the distance G9 be set to a value not less than 0.2 mm and not more than 1.5 mm at the distal end and the proximal end of the blade portion 6. In the first embodiment, the distance G9 is set to, for example, 0.42 mm at the distal end of the blade portion 6 and 0.38 mm at the proximal end of the blade portion 6. As a result, the blade surfaces 9 of the front-face portion 7 of the blade portion 6 are shaped differently from the blade surfaces 10 of the back-face portion 8 of the blade portion 6.

Figure 3A:
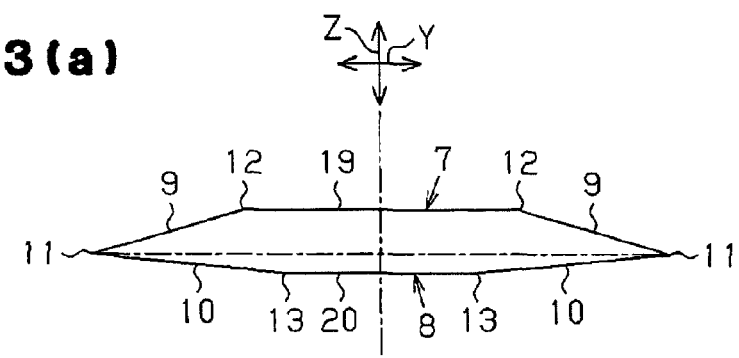
FIG. 3(*a*) is a cross-sectional view taken along line A1-A1 of FIG. 2(*b*)
Figure 3B:
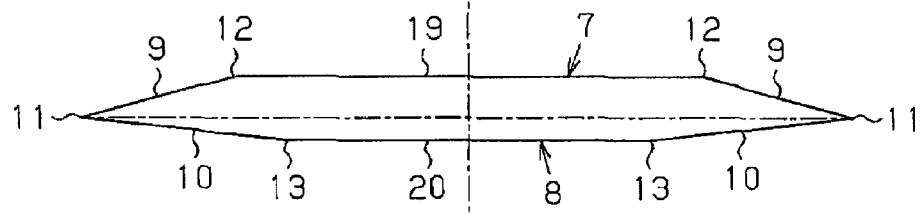
Figure 3C:
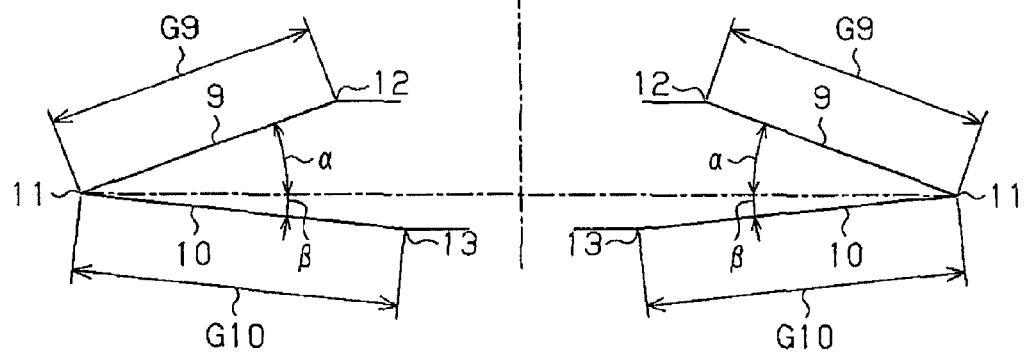

With reference to FIG. 3(c), the inclination angle α between each blade surface 9 of the front-face portion 7 of the blade portion 6 and the plane including the cutting edge 11 in the width direction Y is set to a value greater than the inclination angle β between each blade surface 10 of the back-face portion 8 of the blade portion 6 and the aforementioned plane. The inclination angle β is set to a value not more than a half of the inclination angle α. The inclination angle α is set to a value not less than 10 degrees and not more than 60 degrees and, preferably, not less than 10 degrees and not more than 30 degrees. The inclination angle β is set to a value not less than 3 degrees and not more than 30 degrees and, preferably, not less than 3 degrees and not more than 10 degrees. In the first embodiment, the inclination angle α is set to 20 degrees and the inclination angle β is set to 6 degrees, for example.

Figure 2B:
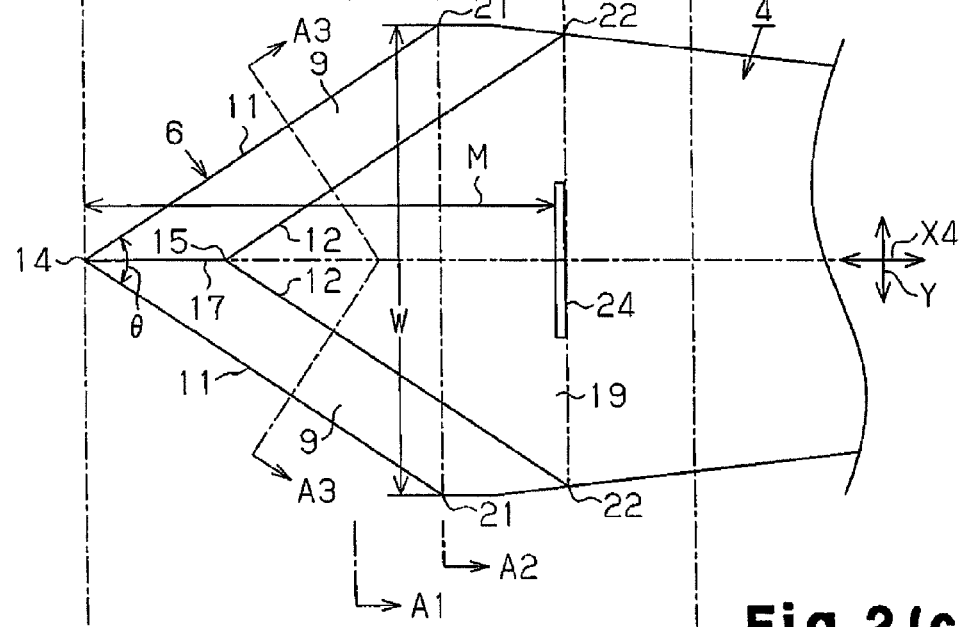
Figure 2C:
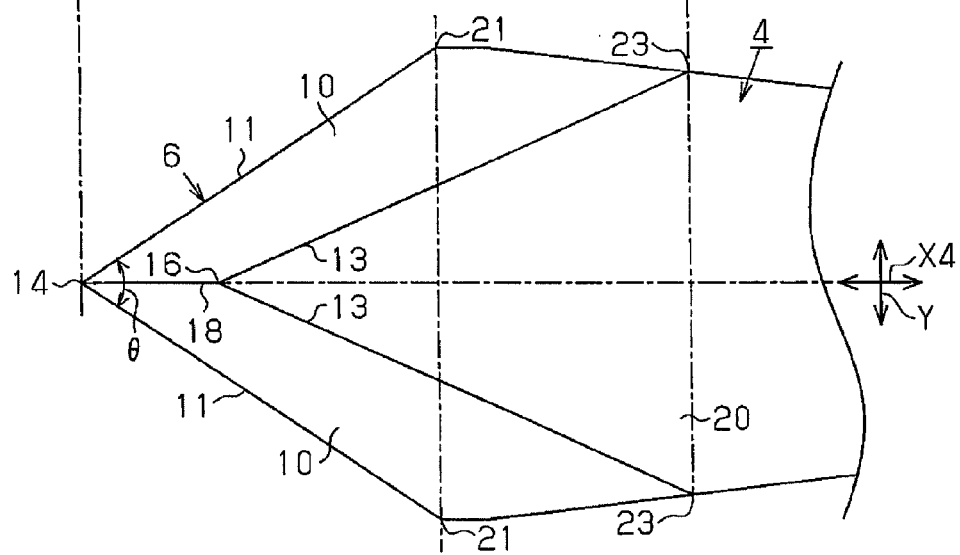

As illustrated in FIGS. 2(b) and 2(c), the separation angle θ between the cutting edges 11 in the width direction Y in the blade portion 6 is set to a value not less than 60 degrees and not more than 120 degrees and, preferably, not less than 60 degrees and not more than 90 degrees. In the first embodiment, the separation angle θ is set to, for example, 67 degrees.

With reference to FIG. 1(b), it is preferable that the length L of the blade plate 4 from the point 14 of the blade portion 6 to the bent portion 5 of the blade plate 4 be set to a value not less than ten times and not more than fifty times the thickness T of the blade plate 4 between the middle surface 19 of the front-face portion 7 of the blade portion 6 and the middle surface 20 of the back-face portion 8 of the blade portion 6. The length L is set to a value not less than 2.5 mm and not more than 10 mm, which is, for example, 6 mm. The thickness T is set to a value not less than 0.05 mm and not more than 1.0 mm, which is, for example, 0.2 mm.

As illustrated in FIG. 2(b), in the blade plate 4, the two cutting edges 11 in the width direction Y of the blade portion 6 have a maximum width-direction distance W between the ends 21 of the cutting edges 11. A linear mark 24 is formed at a position close to the proximal end of the blade portion 6 with respect to the line segment connecting the ends 21 of the cutting edges 11 in the width direction Y to each other. The distance M between the mark 24 and the point 14 and the width-direction distance W between the ends 21 of the cutting edges 11 in the width direction Y are substantially equal. It is preferable that the width-direction distance W and the distance M be set to a value not less than 1.0 mm and not more than 5.0 mm. In the first embodiment, the width-direction distance W and the distance M are set to, for example, 2.4 mm. Alternatively, the linear mark 24 may be arranged at a position on the aforementioned line segment or a position close to the distal end of the blade portion 6 with respect to the line segment.

A cataract surgery using the transconjunctival single-plane sclerocorneal incision method, which has been described in the background of the invention, is carried out in the manner described below, using the medical knife of the first embodiment.

Figure 4A:
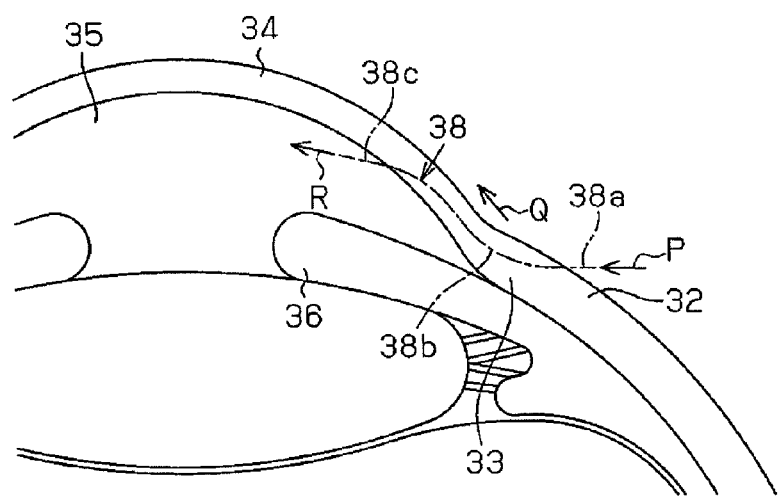
FIG. 4(*a*) is a cross-sectional view showing a portion of the eyeball, illustrating a method of using the medical knife in the transconjunctival single-plane sclerocorneal incision method.
Figure 4B:
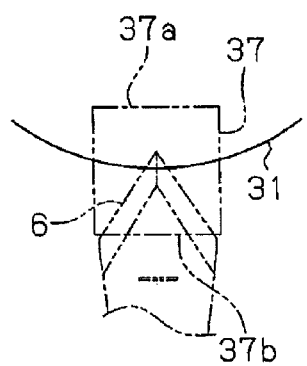
Figure 4C:
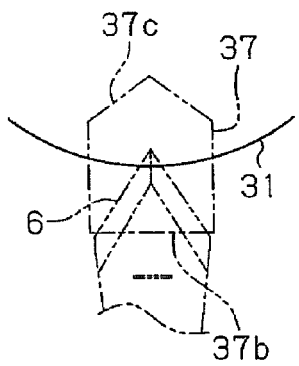
Figure 4D:
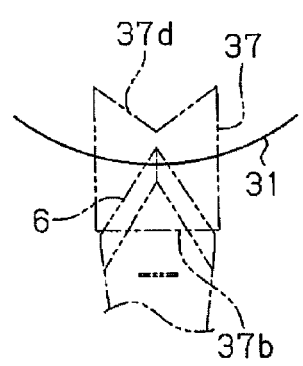

As illustrated in FIG. 4(a), the blade portion 6 moves along a substantially S-shaped movement path 38 while changing its proceeding direction sequentially from a movement path section 38a to a movement path section 38b and then to a movement path section 38c. The movement path section 38a extends in the direction of arrow P to enter the conjunctiva 32. The movement path section 38b extends in the direction of arrow Q to proceed from the sclera 33 to the cornea 34. The movement path section 38c extends in the direction of arrow R to enter the anterior chamber 35. The surface area of each blade surface 10 in the width direction Y of the back-face portion 8 of the blade portion 6 is great in the zone corresponding to the proximal end compared to the zone corresponding to the distal end of the blade portion 6. Accordingly, when upward force (outward force) that presses the blade portion 6 upward is applied to the back-face portion 8, the upward force acts more intensely on the proximal end of the back-face portion 8 than the distal end of the back-face portion 8. With reference to FIG. 2(a), such unevenly acting upward force is likely to generate rotation moment in direction D, in which the proximal end of the blade portion 6 is pressed upward and the distal end of the blade portion 6 is pressed downward. In the front-face portion 7 of the blade portion 6, the surface area of each blade surface 9 in the width direction Y is substantially uniform from the distal end to the proximal end of the blade portion 6. Thus, downward force (inward force) that presses the blade portion 6 downward is less likely to act unevenly and produce rotation moment. As a result, the rotation moment in direction D, in which the proximal end of the blade portion 6 is pressed upward and the distal end of the blade portion 6 is pressed downward, facilitates moving from the movement path section 38b extending in the direction of arrow Q to proceed from the sclera 33 to the cornea 34 to the movement path section 38c extending in the direction of arrow R to enter the anterior chamber 35 in the above-described substantially S-shaped movement path 38, as illustrated in FIG. 4(a).

Figure 6A:
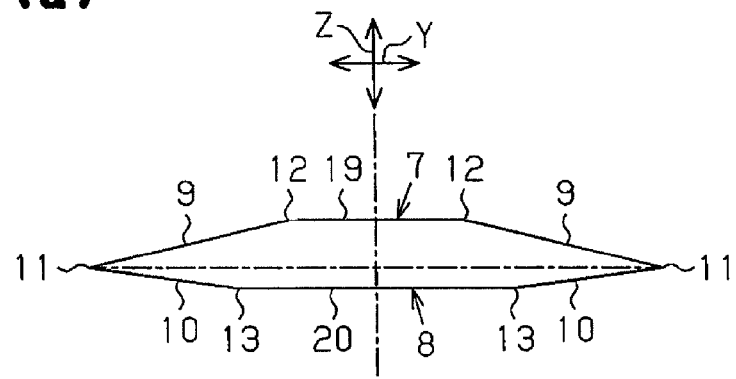
FIG. 6(*a*) is a cross-sectional view taken along line B1-B1 of FIG. 5(*b*)
Figure 6B:
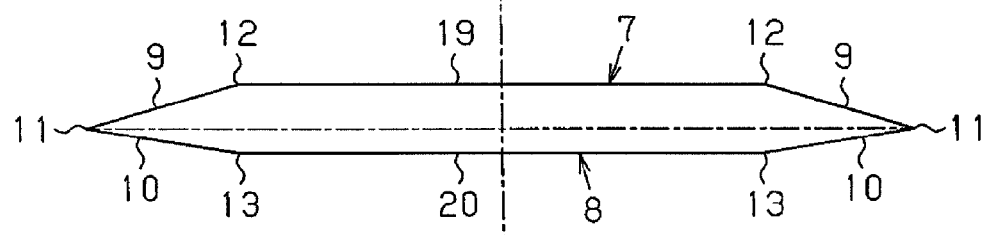

A medical knife according to a second embodiment of the present invention will now be described with reference to FIGS. 5 and 6. The description below is focused on the difference between the first embodiment and the second embodiment.

Unlike the back-face portion 8 of the blade portion 6 in the first embodiment, each blade surface 10 in the width direction Y of the back-face portion 8 of the blade portion 6 is shaped to gradually increase the distance G10 between the opposite side 13 and the cutting edge 11 from the proximal end to the distal end of the blade portion 6, in the opposite direction to the corresponding direction in the case of the back-face portion 8 of the blade portion 6 of the first embodiment. The proximal end of the blade portion 6 corresponds to the line segment connecting the ends 22 of the opposite sides 12 to each other, which is more spaced from the point 14 than the line segment connecting the ends 23 of the opposite sides 13 to each other. It is preferable that the distance G10 be set to a value not less than 0.2 mm and not more than 1.5 mm at the proximal end of the blade portion 6 and a value not less than 0.3 mm and not more than 2.0 mm at the distal end of the blade portion 6. In the second embodiment, the distance G10 is set to, for example, 0.63 mm at the distal end of the blade portion 6 and 0.44 mm at the proximal end of the blade portion 6. As in the front-face portion 7 of the blade portion 6 of the first embodiment, each blade surface 9 in the width direction Y of the front-face portion 7 of the blade portion 6 is shaped to have a substantially uniform distance G9 between the opposite side 12 and the cutting edge 11 throughout the range corresponding to the cutting edge 11 from the distal end to the proximal end of the blade portion 6. It is preferable that the distance G9 be set to a value not less than 0.2 mm and not more than 1.5 mm at the distal end and the proximal end of the blade portion 6. In the second embodiment, the distance G9 is set to, for example, 0.42 mm at the distal end of the blade portion 6 and 0.38 mm at the proximal end of the blade portion 6. As a result, the blade surfaces 9 of the front-face portion 7 of the blade portion 6 are shaped differently from the blade surface 10 of the back-face portion 8 of the blade portion 6.

Figure 6C:
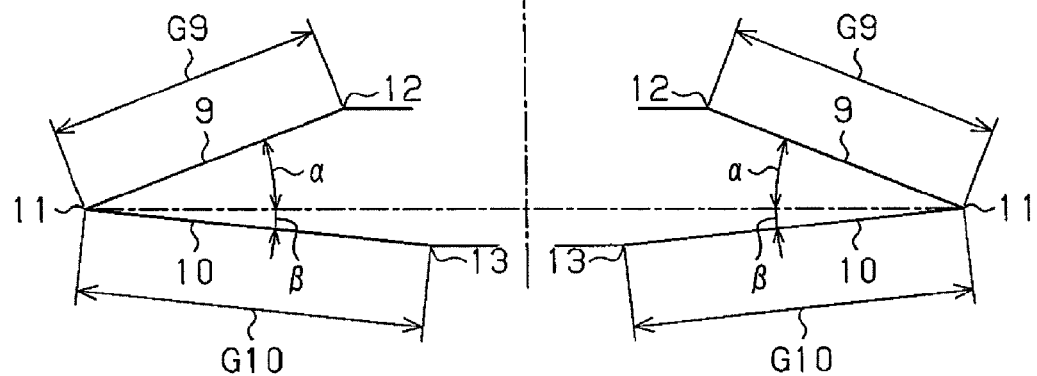

As illustrated in FIG. 6(c), the inclination angle α between each blade surface 9 of the front-face portion 7 of the blade portion 6 and the plane including the cutting edge 11 in the width direction Y is set to a value greater than the inclination angle β between each blade surface 10 of the back-face portion 8 of the blade portion 6 and the aforementioned plane. The inclination angle β is set to a value not more than a half of the inclination angle α. The inclination angle α is set to a value not less than 10 degrees and not more than 60 degrees and, preferably, not less than 10 degrees and not more than 30 degrees. The inclination angle β is set to a value not less than 3 degrees and not more than 30 degrees and, preferably, not less than 3 degrees and not more than 10 degrees. In the second embodiment, the inclination angle α is set to 20 degrees and the inclination angle β is set to 6 degrees, for example.

With reference to FIGS. 5(b) and 5(c), the separation angle θ between the cutting edges 11 in the width direction Y of the blade portion 6 is set to a value not less than 60 degrees and not more than 120 degrees and, preferably, not less than 60 degrees and not more than 90 degrees. In the second embodiment, the separation angle θ is set to, for example, 63 degrees.

It is preferable that the length L of the blade plate 4 be set to a value not less than ten times and not more than fifty times the thickness T of the blade plate 4 between the middle surface 19 of the front-face portion 7 of the blade portion 6 and the middle surface 20 of the back-face portion 8 of the blade portion 6. The length L is set to a value not less than 2.5 mm and not more than 10 mm, which is, for example, 6 mm. The thickness T is set to a value not less than 0.05 mm and not more than 1.0 mm, which is, for example, 0.2 mm.

As illustrated in FIGS. 5(a) and 5(b), in the blade plate 4, the two cutting edges 11 in the width direction Y of the blade portion 6 are gradually inclined from the front-face portion 7 to the back-face portion 8 in the direction from the point 14 to the ends 21. A maximum width-direction distance W is defined between the ends 21 of the cutting edges 11 in the width direction Y. The mark 24 is formed at a position close to the proximal end of the blade portion 6 with respect to the line segment connecting the ends 21 of the cutting edges 11 in the width direction Y to each other. The distance M between the mark 24 and the point 14 and the width-direction distance W between the ends 21 of the cutting edges 11 in the width direction Y are substantially equal. It is preferable that the width-direction distance W and the distance M be set to a value not less than 1.0 mm and not more than 5.0 mm. The width-direction distance W and the distance M are set to, for example, 2.4 mm. Alternatively, the linear mark 24 may be arranged at a position on the aforementioned line segment or a position close to the distal end of the blade portion 6 with respect to the line segment.

A cataract surgery using the transconjunctival single-plane sclerocorneal incision method, which has been described in the background of the invention, is carried out in the manner described below, using the medical knife of the second embodiment.

As illustrated in FIG. 4(a), the blade portion 6 moves along the substantially S-shaped movement path 38 while changing its proceeding direction sequentially from the movement path section 38a to the movement path section 38b and then to the movement path section 38c. The movement path section 38a extends in the direction of arrow P to enter the conjunctiva 32. The movement path section 38b extends in the direction of arrow Q to proceed from the sclera 33 to the cornea 34. The movement path section 38c extends in the direction of arrow R to enter the anterior chamber 35. The surface area of each blade surface 10 in the width direction Y of the back-face portion 8 of the blade portion 6 is great in the zone corresponding to the distal end compared to the zone corresponding to the proximal end of the blade portion 6. As a result, when upward force that presses the blade portion 6 upward is applied to the back-face portion 8, the upward force acts more intensely on the distal end of the back-face portion 8 than the proximal end of the back-face portion 8. With reference to FIG. 5(a), such unevenly acting upward force is likely to generate rotation moment in direction U, in which the distal end of the blade portion 6 is pressed upward and the proximal end of the blade portion 6 is pressed downward. In the front-face portion 7 of the blade portion 6, the surface area of each blade surface 9 in the width direction Y is substantially uniform from the distal end to the proximal end of the blade portion 6. This makes it difficult for the downward force that presses the blade portion 6 downward to act unevenly and produce rotation moment. As a result, the rotation moment in direction U, in which the distal end of the blade portion 6 is pressed upward and the proximal end of the blade portion 6 is pressed downward, facilitates moving from the movement path section 38a extending in the direction of arrow P to enter the conjunctiva 32 to the movement path section 38b extending in the direction of arrow Q to proceed from the sclera 33 to the cornea 34 in the above-described substantially S-shaped movement path 38, as illustrated in FIG. 4(a).

Figure 8A:
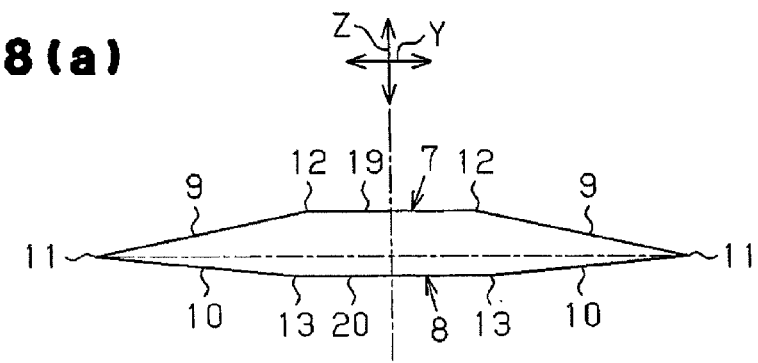
FIG. 8(*a*) is a cross-sectional view taken along line C1-C1 of FIG. 7(*b*)
Figure 8B:
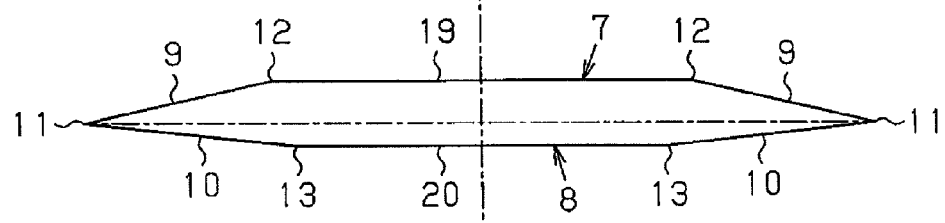
Figure 8C:
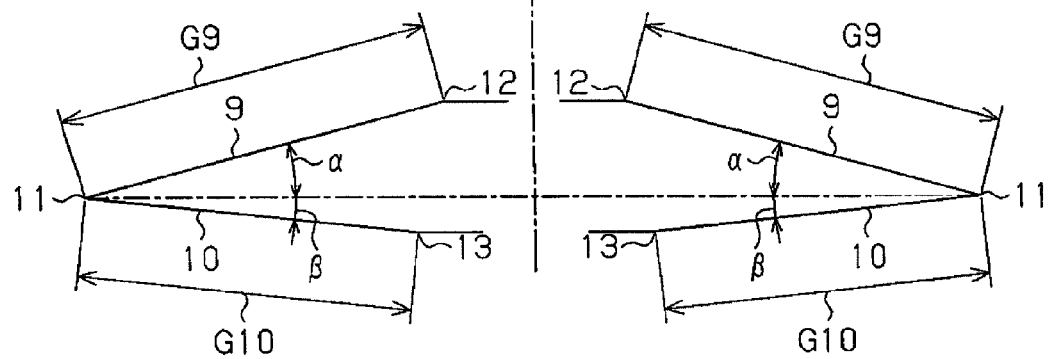

A medical knife according to a third embodiment of the present invention will now be described with reference to FIGS. 7 and 8. The description below is focused on the difference between the first embodiment and the third embodiment.

As in the back-face portion 8 of the blade portion 6 in the first embodiment, each blade surface 10 in the width direction Y of the back-face portion 8 of the blade portion 6 is shaped to gradually increase the distance G10 between the opposite side 13 and the cutting edge 11 from the distal end to the proximal end of the blade portion 6. The blade surfaces 9 in the width direction Y of the front-face portion 7 of the blade portion 6 are different from the corresponding blade surfaces of the front-face portion 7 of the blade portion 6 in the first embodiment. Specifically, the distance G9 between each opposite side 12 and the corresponding cutting edge 11 gradually increases in the direction opposite to the direction in which the distance G10 of each blade surface 10 in the width direction Y of the back-face portion 8 increases, or the direction from the proximal end to the distal end of the blade portion 6, as in the back-face portion 8 of the blade portion 6 in the second embodiment. In other words, the distance G10 gradually decreases from the distal end to the proximal end of the blade portion 6. The proximal end of the blade portion 6 corresponds to the line segment connecting the ends 23 of the opposite sides 13 to each other, which is more spaced from the point 14 than the line segment connecting the ends 22 of the opposite sides 12 to each other. As a result, the blade surfaces 9 of the front-face portion 7 of the blade portion 6 are shaped differently from the blade surfaces 10 of the back-face portion 8 of the blade portion 6. The cutting edges 11 in the width direction Y of the blade portion 6 are gradually inclined from the back-face portion 8 to the front-face portion 7 in the direction from the point 14 to the ends 21, as in the first embodiment.

A cataract surgery using the transconjunctival single-plane sclerocorneal incision method, which has been described in the background of the invention, is performed in the manner described below, using the medical knife of the third embodiment.

As illustrated in FIG. 4(a), the blade portion 6 moves along the substantially S-shaped movement path 38 while changing its proceeding direction sequentially from the movement path section 38*a* to the movement path section 38*b* and then to the movement path section 38*c*. The movement path section 38*a* extends in the direction of arrow P to enter the conjunctiva 32. The movement path section 38*b* extends in the direction of arrow Q to proceed from the sclera 33 to the cornea 34. The movement path section 38*c* extends in the direction of arrow R to enter the anterior chamber 35. The surface area of each blade surface 10 in the width direction Y of the back-face portion 8 of the blade portion 6 is great in the zone corresponding to the proximal end compared to the zone corresponding to the distal end of the blade portion 6. As a result, when upward force that presses the blade portion 6 upward is applied to the back-face portion 8, the upward force acts more intensely on the proximal end of the back-face portion 8 than the distal end of the back-face portion 8. With reference to FIG. 7(*a*), such unevenly acting upward force is likely to generate rotation moment in direction D, in which the proximal end of the blade portion 6 is pressed upward and the distal end of the blade portion 6 is pressed downward. In the front-face portion 7 of the blade portion 6, the surface area of each blade surface 9 in the width direction Y is great in the zone corresponding to the distal end compared to the zone corresponding to the proximal end of the blade portion 6. As a result, when downward force that presses the blade portion 6 downward is applied to the front-face portion 7, the downward force acts more intensely on the distal end of the front-face portion 7 than the proximal end of the front-face portion 7. Such unevenly acting downward force is likely to generate rotation moment in direction D, in which the distal end of the blade portion 6 is pressed downward and the proximal end of the blade portion 6 is pressed upward. As a result, the rotation moment in direction D, in which the proximal end of the blade portion 6 is pressed upward and the distal end of the blade portion 6 is pressed downward, acts simultaneously on the back-face portion 8 and the front-face portion 7 of the blade portion 6 and facilitates moving from the movement path section 38*b* extending in the direction of arrow Q to proceed from the sclera 33 to the cornea 34 to the movement path section 38*c* extending in the direction of arrow R to enter the anterior chamber 35 in the above-described substantially S-shaped movement path 38, as illustrated in FIG. 4(*a*).

Figure 9A:
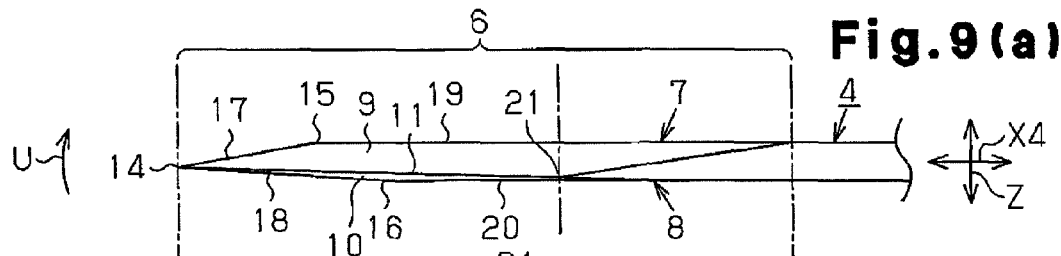
FIG. 9(*a*) is an enlarged front view showing a portion of a blade portion of a medical knife according to a fourth embodiment of the invention.
Figure 9B:
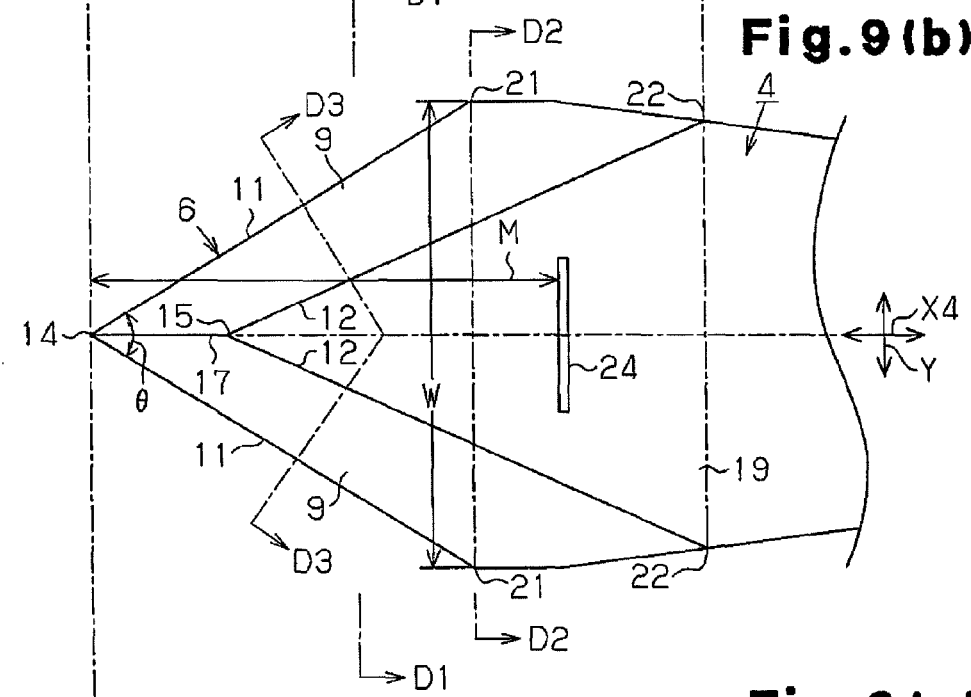
Figure 9C:
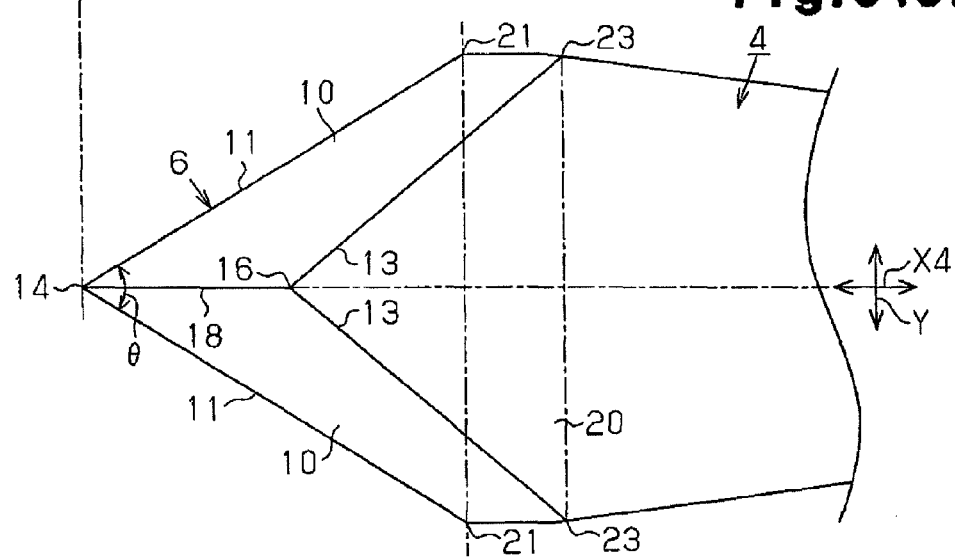
Figure 10A:
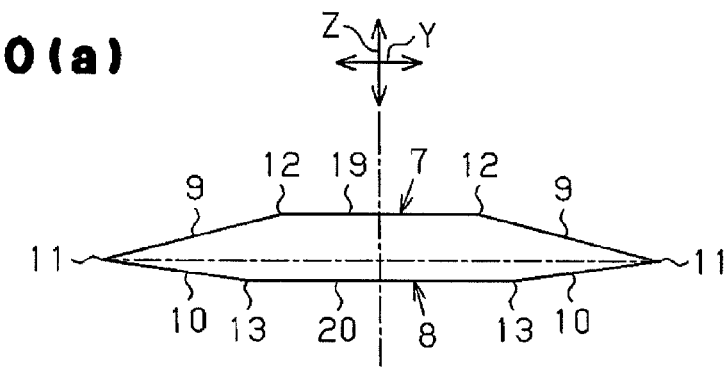
FIG. 10(*a*) is a cross-sectional view taken along line D1-D1 of FIG. 9(*b*)
Figure 10B:
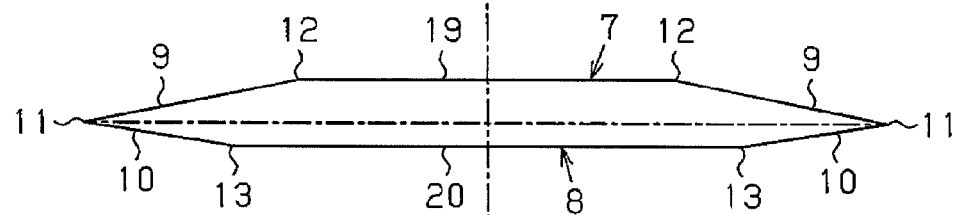
Figure 10C:
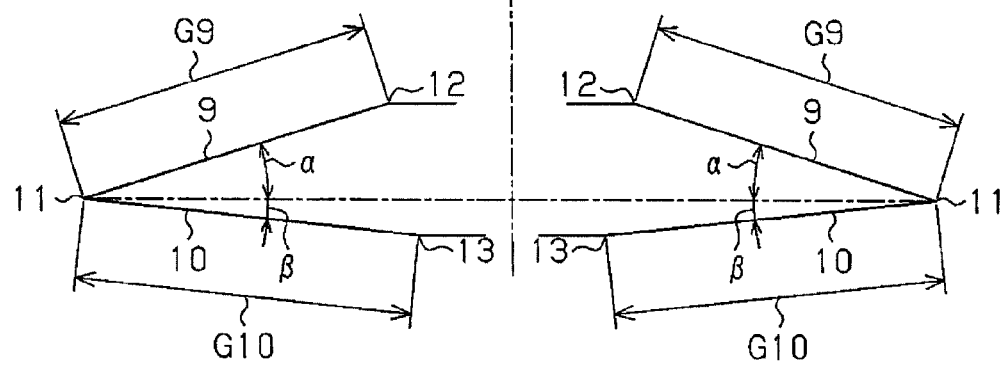

A medical knife according to a fourth embodiment of the present invention will now be described with reference to FIGS. 9 and 10. The description below is focused on the difference between the first embodiment and the fourth embodiment.

As in the back-face portion 8 of the blade portion 6 in the second embodiment, each blade surface 10 in the width direction Y of the back-face portion 8 of the blade portion 6 is shaped to gradually increase the distance G10 between the opposite side 13 and the cutting edge 11 from the proximal end to the distal end of the blade portion 6. In this case, the proximal end of the blade portion 6 corresponds to the line segment connecting the ends 22 of the opposite sides 12 to each other, which is more spaced from the point 14 than the line segment connecting the ends 23 of the opposite sides 13 to each other. The blade surfaces 9 in the width direction Y of the front-face portion 7 of the blade portion 6 are different from the corresponding blade surfaces of the front-face portion 7 of the blade portion 6 in the second embodiment. Specifically, the distance G9 between each opposite side 12 and the corresponding cutting edge 11 gradually increases in the direction opposite to the direction in which the distance G10 of each blade surface 10 in the width direction Y of the back-face portion 8 increases, or the direction from the distal end to the proximal end of the blade portion 6, as in the back-face portion 8 of the blade portion 6 in the first embodiment. In other words, the distance G9 gradually decreases from the proximal end to the distal end of the blade portion 6. As a result, the blade surfaces 9 of the front-face portion 7 of the blade portion 6 are shaped differently from the blade surfaces 10 of the back-face portion 8 of the blade portion 6. As in the second embodiment, the cutting edges 11 in the width direction Y of the blade portion 6 are gradually inclined from the front-face portion 7 to the back-face portion 8 in the direction from the point 14 to the ends 21.

A cataract surgery using the transconjunctival single-plane sclerocorneal incision method, which has been described in the background of the invention, is carried out in the manner described below, using the medical knife of the fourth embodiment.

As illustrated in FIG. 4(*a*), the blade portion 6 moves along the substantially S-shaped movement path 38 while changing its proceeding direction sequentially from the movement path section 38*a* to the movement path section 38*b* and then to the movement path section 38*c*. The movement path section 38*a* extends in the direction of arrow P to enter the conjunctiva 32. The movement path section 38*b* extends in the direction of arrow Q to proceed from the sclera 33 to the cornea 34. The movement path section 38*c* extends in the direction of arrow R to enter the anterior chamber 35. The surface area of each blade surface 10 in the width direction Y of the back-face portion 8 of the blade portion 6 is great in the zone corresponding to the distal end compared to the zone corresponding to the proximal end of the blade portion 6. As a result, when upward force that presses the blade portion 6 upward is applied to the back-face portion 8 the upward force acts more intensely on the distal end of the back-face portion 8 than the proximal end of the back-face portion 8. With reference to FIG. 9(*a*), such unevenly acting upward force is likely to generate rotation moment in direction U, in which the distal end of the blade portion 6 is pressed upward and the proximal end of the blade portion 6 is pressed downward. In the front-face portion 7 of the blade portion 6, the surface area of each blade surface 9 in the width direction Y is great in the zone corresponding to the proximal end compared to the zone corresponding to the distal end of the blade portion 6. As a result, when downward force that presses the blade portion 6 downward is applied to the front-face portion 7, the downward force acts more intensely on the proximal end of the front-face portion 7 than the distal end of the front-face portion 7. Such unevenly acting downward force is likely to generate rotation moment in direction U, in which the proximal end of the blade portion 6 is pressed downward and the distal end of the blade portion 6 is pressed upward. As a result, the rotation moment in direction U, in which the distal end of the blade portion 6 is pressed upward and the proximal end of the blade portion 6 is pressed downward, acts simultaneously on the back-face portion 8 and the front-face portion 7 of the blade portion 6 and facilitates moving from the movement path section 38*a* extending in the direction of arrow P to enter the conjunctiva 32 to the movement path section 38*b* extending in the direction of arrow Q to proceed from the sclera 33 to the cornea 34 in the above-described substantially S-shaped movement path 38, as illustrated in FIG. 4(*a*).

Figure 11:
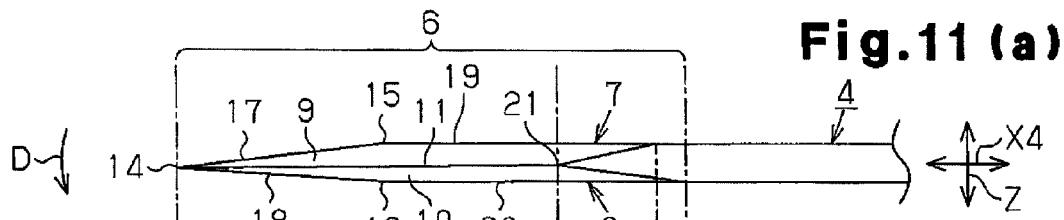
FIG. 11(*a*) is an enlarged front view showing a portion of a blade portion of a medical knife according to a fifth embodiment of the invention.
Figure 11:
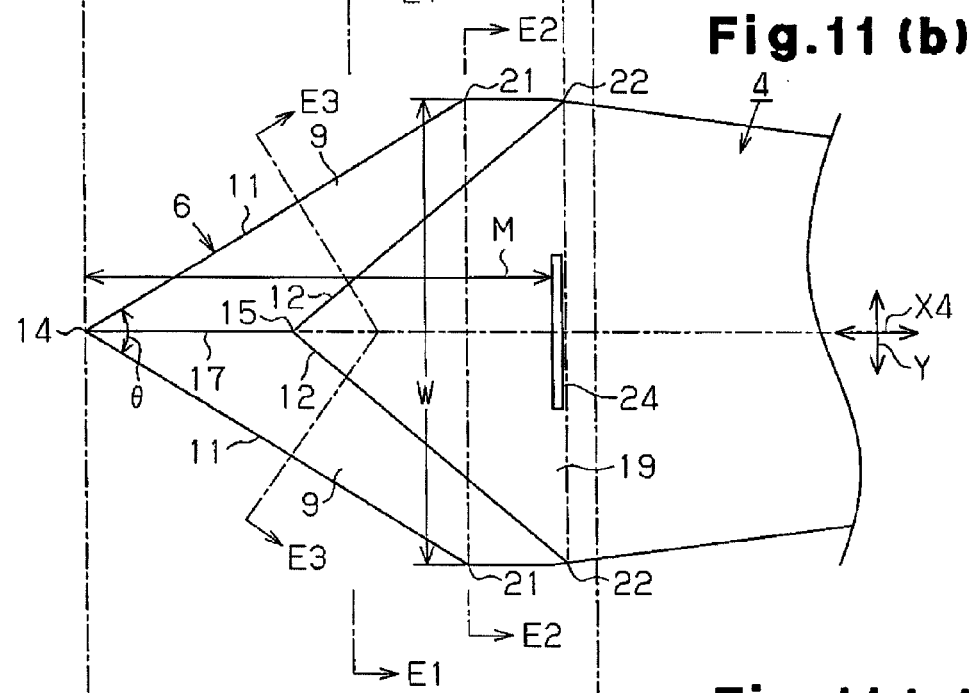
Figure 11:
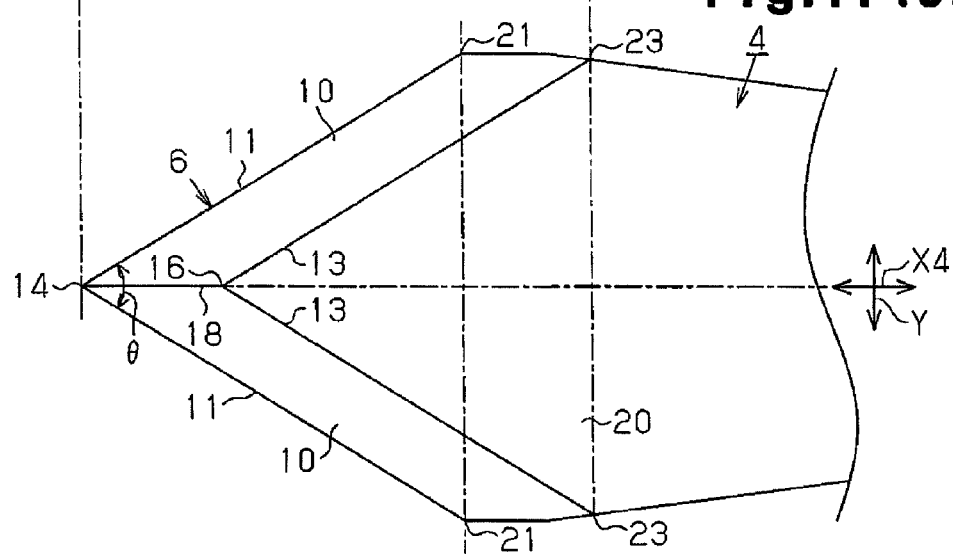
Figure 12A:
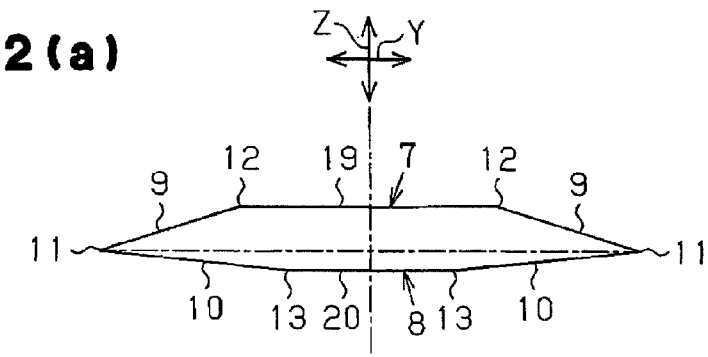
FIG. 12(a) is a cross-sectional view taken along line E1-E1 of FIG. 11(b)
Figure 12B:
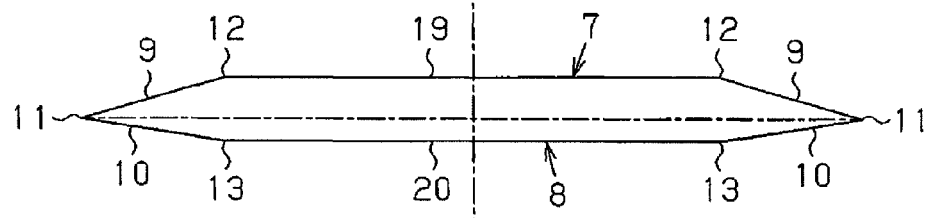
FIG. 12(b) is a cross-sectional view taken along line E2-E2 of FIG. 11(b)
Figure 12C:
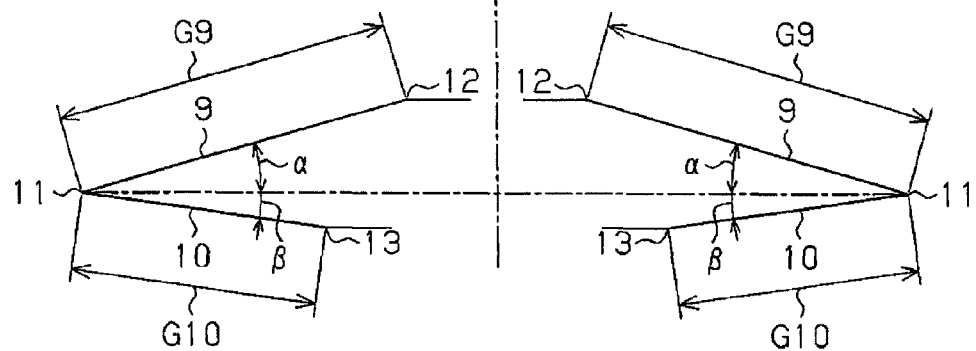
FIG. 12(c) is a cross-sectional view taken along line E3-E3 of FIG. 11(b).

A medical knife according to a fifth embodiment of the present invention will now be described with reference to FIGS. 11 and 12. The description below is focused on the difference between the first embodiment and the fifth embodiment.

Each blade surface 10 in the width direction Y of the back-face portion 8 of the blade portion 6 is shaped to have a substantially uniform distance G10 between the opposite side 13 and the cutting edge 11 throughout the range corresponding to the cutting edge 11 from the distal end to the proximal end of the blade portion 6, as in the front-face portion 7 of the blade portion 6 in the first and second embodiments. In this case, the range from the distal end to the proximal end of the blade portion 6 corresponds to the line segment connecting the ends 23 of the opposite sides 13 to each other, which is more spaced from the point 14 than the line segment connecting the ends 22 of the opposite sides 12 to each other. As in the back-face portion 8 of the blade portion 6 in the second embodiment and the front-face portion 7 of the blade portion 6 in the third embodiment, each blade surface 9 in the width direction Y of the front-face portion 7 of the blade portion 6 in the fifth embodiment is shaped to gradually increase the distance G9 between the opposite side 12 and the cutting edge 11 from the proximal end to the distal end of the blade portion 6. As in the first embodiment, the cutting edges 11 in the width direction Y of the blade portion 6 are gradually inclined from the point 14 to the ends 21 in the direction from the back-face portion 8 to the front-face portion 7.

A cataract surgery using the transconjunctival single-plane sclerocorneal incision method, which has been described in the background of the invention, is performed in the manner described below, using the medical knife of the fifth embodiment.

As illustrated in FIG. 4(a), the blade portion 6 moves along the substantially S-shaped movement path 38 while changing its proceeding direction sequentially from the movement path section 38a to the movement path section 38b and then to the movement path section 38c. The movement path section 38a extends in the direction of arrow P to enter the conjunctiva 32. The movement path section 38b extends in the direction of arrow Q to proceed from the sclera 33 to the cornea 34. The movement path section 38c extends in the direction of arrow R to enter the anterior chamber 35. The surface area of each blade surface 9 in the width direction Y of the front-face portion 7 of the blade portion 6 is great in the zone corresponding to the distal end compared to the zone corresponding to the proximal end of the blade portion 6. As a result, when downward force that presses the blade portion 6 downward is applied to the front-face portion 7, the downward force acts more intensely on the distal end of the front-face portion 7 than the proximal end of the front-face portion 7. With reference to FIG. 11(a), such unevenly acting downward force easily generates rotation moment in direction D, in which the distal end of the blade portion 6 is pressed downward and the proximal end of the blade portion 6 is pressed upward. In the back-face portion 8 of the blade portion 6, the surface area of each blade surface 10 in the width direction Y is substantially uniform from the distal end to the proximal end of the blade portion 6. This makes it difficult for the upward force that presses the blade portion 6 upward to act unevenly and produce rotation moment. As a result, the rotation moment in direction D, in which the distal end of the blade portion 6 is pressed downward and the proximal end of the blade portion 6 is pressed upward, facilitates moving from the movement path section 38b extending in the direction of arrow Q to proceed from the sclera 33 to the cornea 34 to the movement path section 38c extending in the direction of arrow R to enter the anterior chamber 35 in the above-described substantially S-shaped movement path 38, as illustrated in FIG. 4(a).

The illustrated embodiments have the advantages described below.

(1) In a cataract surgery using the transconjunctival single-plane sclerocorneal incision method in the first, third, and fifth embodiments, the operator moves the blade portion 6 while following the movement path 38, which is substantially S-shaped, from the vicinity of the limbus 31 into the anterior chamber 35 via the conjunctiva 32, the sclera 33, and the cornea 34. This allows the operator to smoothly move the blade portion 6 with less resistance from the movement path section 38b extending in the direction of arrow Q to proceed from the sclera 33 to the cornea 34 to the movement path section 38c extending in the direction of arrow R to enter the anterior chamber 35. As a result, the substantially S-shaped incision wound 37 exhibiting improved self-sealing performance is easily formed. Also, the blade portion 6 linearly enters the anterior chamber 35 along the movement path section 38c extending in the direction of arrow R without being translated upward or downward. The inner incision line 37a of the incision wound 37 is thus prevented from having a projected shape and is easily formed in a linear shape.

(2) In a cataract surgery using the transconjunctival single-plane sclerocorneal incision method in the second and fourth embodiments, the operator moves the blade portion 6 while following the movement path 38, which is substantially S-shaped, from the vicinity of the limbus 31 into the anterior chamber 35 via the conjunctiva 32, the sclera 33, and the cornea 34. This allows the operator to smoothly move the blade portion 6 with less resistance from the movement path section 38a extending in the direction of arrow P to enter the conjunctiva 32 to the movement path section 38b extending in the direction of arrow Q to proceed from the sclera 33 to the cornea 34. As a result, the substantially S-shaped incision wound 37 exhibiting improved self-sealing performance is easily formed.

(3) In a cataract surgery using the transconjunctival single-plane sclerocorneal incision method in the first to fifth embodiments, the operator moves the blade portion 6 while following the movement path 38, which is substantially S-shaped, from the vicinity of the limbus 31 into the anterior chamber 35 via the conjunctiva 32, the sclera 33, and the cornea 34. Specifically, when the mark 24 formed on the middle surface 19 of the front-face portion 7 of the blade portion 6 reaches the outer incision line 37b of the incision wound 37, the point 14 of the blade portion 6 enters the anterior chamber 35. As the blade portion 6 proceeds continuously, the inner incision line 37a is formed in a substantially linear shape. As a result, the shape of the incision wound 37 as a whole, which is formed between the inner incision line 37a and the outer incision line 37b, substantially becomes a square. This improves self-sealing performance of the incision wound 37.

The present invention may be configured in any other suitable forms than the illustrated embodiments, including the forms described below.

In the front-face portion 7 of the blade portion 6 in the first and second embodiments and the back-face portion 8 of the blade portion 6 in the fifth embodiment, the blade surfaces 9 in the width direction Y of the front-face portion 7 and the blade surfaces 10 in the width direction Y of the back-face portion 8 are each formed to have a substantially uniform distance G9, G10 between the opposite side 12, 13 and the cutting edge 11 throughout the range corresponding to the cutting edge 11 from the distal end to the proximal end of the blade portion 6. However, the blade surfaces 9, 10 may be formed such that the distance G9, G10 between the opposite side 12, 13 and the cutting edge 11 becomes substantially equal at least in a zone corresponding to the distal end of the cutting edge 11 and a zone corresponding to the proximal end of the cutting edge 11, out of the whole range corresponding to the cutting edge 11 from the distal end to the proximal end of the blade portion 6. Alternatively, each cutting edge 11 may be curved inward (toward the opposite side 12, 13) or outward in a zone corresponding to a middle portion of the cutting edge 11, which is between the zone corresponding to the distal end of the cutting edge 11 and the cone corresponding to the proximal end of the cutting edge 11. The distance G9, G10 between the opposite side 12, 13 and the cutting edge 11 in the zone corresponding to the middle portion of the cutting edge 11 thus becomes different from the distance G9, G10 in the zones corresponding to the distal and proximal ends of the cutting edge 11. According to these configurations, rotation moment is unlikely to be generated by unevenly acting downward or upward force that presses the blade portion 6 downward or upward.

In the first to fifth embodiments, each blade surface 9, 10 in the width direction Y may be not only shaped flat but also curved inward or outward between the cutting edge 11 and the opposite side 12, 13.

In the front-face portion 7 and the back-face portion 8 in the first to fifth embodiments, the middle surfaces 19, 20 may be not only shaped flat but also curved inward or outward.

In the first to fifth embodiments, the cutting edge 11 of each blade surface 9, 10 in the width direction Y may be inward (toward the opposite side 12, 13) or outward. Alternatively, the opposite side 12, 13 of each blade surface 9, 10 in the width direction Y may be curved outward (toward the cutting edge 11) or inward.

In the first to fifth embodiments, the point 14, at which the cutting edges 11 of the blade surfaces 9, 10 in the width direction Y cross each other, may have a slightly round shape.

In the back-face portion 8 of the blade portion 6 in the first to third embodiments and the front-face portion 7 of the blade portion 6 in the fourth embodiment, the boundary 17, 18 between the point 14 and the peak 15, 16 may be eliminated such that the point 14 coincides with the peak 15, 16. Alternatively, the boundary 17, 18 may be shortened by arranging the peak 15, 16 closer to the point 14.

In the blade plate 4 of the first to fifth embodiments, a plurality of blade portions including the first blade portion 6 having the cutting edge 11, other than the first blade portion 6, may be arranged sequentially from the distal end to the proximal end of the blade plate 4. For example, when the blade plate 4 includes the first blade portion 6 and a second blade portion, one of the separation angle θ between the cutting edges 11 in the width direction Y of the first blade portion 6 and the separation angle between the cutting edges in the width direction of the second blade portion may be greater than the other. Alternatively, the separation angles may be substantially equal.

In the first to fifth embodiments, the blade plate 4 and the support plate 3 of the handle 1 may be formed of any suitable metal other than stainless steel, including titanium and titanium alloy or any suitable material other than metal, such as ceramic or single-crystal silicon or diamond.

In the first to fifth embodiments, the mark 24 may be formed in any suitable shape other than the linear shape, such as a set of two or more separate points, line segments, or a geometric pattern.

In the first to fifth embodiments, a coating layer formed of silicone resin, fluorine resin, or diamond-like carbon may be formed on the outer surfaces of the blade portion 6, as a whole, including the front-face portion 7 and the back-face portion 8. Alternatively, surface roughness adjustment may be performed on the outer surfaces of the blade portion 6 as a whole. Also, the outer surfaces of the blade portion 6 as a whole may be coated with a coating layer that does not reflect light or is resistant to light reflection. This suppresses light reflection by the outer surfaces of the blade portion 6 as a whole caused by illumination in a surgery.

The medical knives in the first to fifth embodiments may be employed in any suitable incision method other than the transconjunctival single-plane sclerocorneal incision method for a cataract surgery, such as a corneal or scleral incision method, or any suitable surgery on the eyeball other than the cataract surgery.

The invention claimed is:

1. A medical knife comprising:
a handle having a grip portion and extending in one direction;
a blade plate extending from the handle in a manner intersecting the handle, the blade plate including a distal end and a proximal end; and
a blade portion formed at the distal end of the blade plate, wherein
the blade portion has a front-face portion and a back-face portion, the front-face portion being formed on an upper side in a thickness direction of the blade plate where the grip portion is arranged, the back-face portion being formed on a lower side in the thickness direction of the blade plate opposite to the grip portion,
four blade surfaces in total are formed at two sides in a width direction of the blade plate intersecting the thickness direction of the blade portion in both the front-face portion and the back-face portion of the blade portion, each side in the front-face portion having a single blade surface, each side in the back-face portion having a single blade surface, the blade surfaces being inclined from a middle portion in the width direction to opposite outer ends in the width direction in the blade plate to cooperatively decrease a thickness dimension,
an outer end at which each one of the blade surfaces of the front-face portion and the corresponding one of the blade surfaces of the back-face portion cross each other form a cutting edge extending from the distal end to the proximal end of the blade portion,
each blade surface of the front-face portion and the back-face portion is defined by the corresponding cutting edge and an opposite side formed on the front-face portion and the back-face portion,
the two blade surfaces in the width direction of the back-face portion of the blade portion are formed to gradually increase a distance between the opposite side and the cutting edge from one of the distal end and the proximal end to the other, and
the two blade surfaces in the width direction of the front-face portion of the blade portion are formed such that the distance between the opposite side and the cutting edge becomes uniform over the entire cutting edge from the distal end to the proximal end of the cutting edge, in the front-face portion and the back-face portion of the blade portion, a boundary between the opposite blade surfaces in the width direction is formed between a point at which the cutting edges of the blade surfaces in the width direction cross each other and a peak at which the opposite sides of the blade surfaces in the width direction cross each other, a middle surface being formed between the opposite sides of the blade surfaces in the width direction, in the blade plate, the cutting edges in the width direction of the blade portion extend from the point to an end, a maximum width-direction distance is defined between the ends of the cutting edges in the width direction, the distance between the opposite side and the cutting edge in each blade surface in the width direction of the back-face portion of the blade portion is greater than the distance between the opposite side and the cutting edge in each blade surface in the width direction of the front-face portion of the blade portion, and the inclination angle between each blade surface of the front-face portion of the blade portion and a plane including the cutting edge in the width direction is set to a value greater than the inclination angle between each blade surface of the back-face portion of the blade portion and said plane.

2. The medical knife according to claim 1, wherein the blade plate is bent toward the front-face portion of the blade portion with respect to the handle, and a length of the blade plate from the distal end to the proximal end of the blade portion is set to a value not less than ten times and not more than fifty times the thickness of the blade plate.

3. The medical knife according to claim 1, wherein in the blade portion, a separation angle between the cutting edges in the width direction is set to a value not less than 60 degrees and not more than 120 degrees.

4. The medical knife according to claim 1, wherein the two blade surfaces in the width direction of the back-face portion of the blade portion are formed to gradually increase the distance between the opposite side and the cutting edge from the distal end to the proximal end.

5. The medical knife according to claim 1, wherein the two blade surfaces in the width direction of the back-face portion of the blade portion are formed to gradually increase the distance between the opposite side and the cutting edge from the proximal end to the distal end.

6. The medical knife according to claim 1, wherein a mark is formed on a line segment connecting the ends of the cutting edges in the width direction to each other or on a proximal or distal side with respect to the line segment, and the distance between the mark and the point and the width-direction distance between the ends of the cutting edges in the width direction are equal to each other.

7. The medical knife according to claim 1, wherein the middle surface of the front-face portion of the blade portion and the middle surface of the back-face portion of the blade portion is formed parallel to each other.

8. The medical knife according to claim 1, wherein the blade surfaces in the width direction is shaped symmetrical with respect to a plane in the thickness direction including the boundary between the blade surfaces in the width direction.

9. The medical knife according to claim 1, wherein the inclination angle of each blade surface of the back-face portion of the blade portion is set to a value not more than a half of the inclination angle of each blade surface of the front-face portion of the blade portion.

* * * * *